United States Patent
Tong et al.

(10) Patent No.: US 12,386,002 B2
(45) Date of Patent: Aug. 12, 2025

(54) CALIBRATION METHODS AND SYSTEMS FOR MEDICAL IMAGING

(71) Applicant: SHANGHAI UNITED IMAGING HEALTHCARE CO., LTD., Shanghai (CN)

(72) Inventors: Li Tong, Shanghai (CN); Tao Sun, Shanghai (CN); Yang Xin, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 445 days.

(21) Appl. No.: 17/664,213

(22) Filed: May 19, 2022

(65) Prior Publication Data

US 2023/0181146 A1    Jun. 15, 2023

(30) Foreign Application Priority Data

Dec. 14, 2021   (CN) .......................... 202111527838.2

(51) Int. Cl.
*A61B 6/58*    (2024.01)
*A61B 6/00*    (2006.01)
*G06T 5/00*    (2006.01)

(52) U.S. Cl.
CPC ............ *A61B 6/582* (2013.01); *A61B 6/5258* (2013.01); *G06T 5/00* (2013.01); *G06T 2207/20081* (2013.01)

(58) Field of Classification Search
CPC ......... A61B 6/582; A61B 6/5258; G06T 5/00; G06T 2207/20081
USPC ....................................................... 382/128
See application file for complete search history.

(56) References Cited

U.S. PATENT DOCUMENTS

| | | | |
|---|---|---|---|
| 10,705,170 B1 | 7/2020 | Wu et al. | |
| 2008/0030789 A1* | 2/2008 | McElvain | H04N 1/506 358/1.9 |
| 2015/0302570 A1* | 10/2015 | Shirakyan | G06T 7/50 348/46 |
| 2021/0156940 A1 | 5/2021 | Sommer et al. | |
| 2021/0350174 A1* | 11/2021 | Merkle | G06T 5/92 |
| 2021/0364587 A1 | 11/2021 | De Weerdt et al. | |

FOREIGN PATENT DOCUMENTS

| | | |
|---|---|---|
| CN | 110244246 A | 9/2019 |
| CN | 111443318 A | 7/2020 |
| CN | 112150574 A | 12/2020 |

* cited by examiner

*Primary Examiner* — Gabriel I Garcia
(74) *Attorney, Agent, or Firm* — METIS IP LLC

(57) ABSTRACT

The present disclosure discloses a calibration method and system for medical imaging. The calibration method comprising: obtaining imaging data; dividing the imaging data into a plurality of patches; and calibrating the imaging data based on one or more target patches of the plurality of patches, wherein the one or more target patches is a part of the plurality of patches.

20 Claims, 15 Drawing Sheets

Label 0: a labeled image block includes no artifact

Label 1: a labeled image block includes artifact

CALIBRATION METHODS AND SYSTEMS FOR MEDICAL IMAGING

CROSS-REFERENCE TO RELATED APPLICATION

This application claims priority to Chinese Patent Application No. 202111527838.2, filed on Dec. 14, 2021, the contents of which are hereby incorporated by reference.

TECHNICAL FIELD

The present disclosure generally relates to medical imaging, and in particular, to calibration systems and methods for medical imaging.

BACKGROUND

Medical imaging is widely used in medical diagnosis and treatment. Due to system errors and device anomalies, some abnormal points may exist in imaging data collected in medical imaging, resulting in artifacts in generated medical images and affecting doctors' diagnoses. Taking magnetic resonance imaging (MRI) as an example, due to external interferences or system faults in scanning, artifacts may exist in MRI images obtained by an MRI device, which may appear as random spots with abnormally large intensities in K-space data. Common system faults may include poor contact of electronic switches or other components during sampling by a high-speed analog-to-digital converter (ADC), a wire tip discharge, etc. Common external interferences may include an instantaneous radio frequency (RF) signal crosstalk of a wireless transmitting device, etc.

Therefore, it is desirable to provide a calibration method for medical imaging, which can correct artifacts and improve imaging quality.

SUMMARY

According to some embodiments of the present disclosure, a calibration method. The calibration method comprising: obtaining imaging data; dividing the imaging data into a plurality of patches; and calibrating the imaging data based on one or more target patches of the plurality of patches, wherein the one or more target patches is a part of the plurality of patches.

In some embodiments, wherein the one or more target patches include one or more abnormal points; and the calibrating the imaging data based on the one or more target patches of the plurality of patches comprises: determining the one or more target patches by processing the plurality of patches using at least one trained first classification model; calibrating the imaging data by calibrating the one or more target patches.

In some embodiments, wherein the imaging data includes K-space data, the determining the one or more target patches by processing the plurality of patches using at least one trained first classification model comprises: generating a reconstructed image based on the K-space data; determining whether the reconstructed image includes artifacts; and determining the one or more target patches by processing the plurality of patches using the at least one trained first classification model based on a determination result of whether the reconstructed image includes artifacts.

In some embodiments, wherein the determining whether the reconstructed image includes artifacts comprises: cropping at least one image block from the reconstructed image; and determining whether the reconstructed image includes artifacts by processing the at least one image block using a trained second classification model.

In some embodiments, wherein the calibrating the imaging data by calibrating the one or more target patches comprises: obtaining one or more calibrated target patches by calibrating the one or more target patches using a trained artifact calibration model; calibrating the imaging data based on the one or more calibrated target patches.

In some embodiments, wherein the calibrating the imaging data by calibrating the one or more target patches comprises: segmenting the one or more abnormal points from the one or more target patches by using an abnormal point segmentation model; and calibrating the imaging data based on a segmentation result of the one or more abnormal points.

In some embodiments, wherein the determining the one or more target patches by processing the plurality of patches using the at least one trained first classification model comprises: determining multiple sets of input data based on position information indicating positions of the plurality of patches in the imaging data; and determining the one or more target patches by inputting the multiple sets of input data into the at least one trained first classification model, respectively.

In some embodiments, wherein the at least one trained first classification model includes a Vision Transformer deep learning model.

In some embodiments, wherein the determining the one or more target patches by processing the plurality of patches using the at least one trained first classification model comprises: preprocessing the plurality of patches; and determining the one or more target patches by processing the plurality of preprocessed patches using the at least one trained first classification model.

In some embodiments, wherein preprocessing the plurality of patches comprises: for each patch of the plurality of patches, determining a preprocessing parameter of the patch based on position information indicating a position of the patch in the imaging data; and preprocessing the patch based on the preprocessing parameter of the patch.

In some embodiments, wherein the calibrating the imaging data based on the one or more target patches of the plurality of patches comprises: calibrating the imaging data by inputting the plurality of patches into a trained patch calibration model, wherein the trained patch calibration model is configured to determine and calibrate the one or more target patches.

In some embodiments, wherein the calibrating the imaging data by inputting the plurality of patches into the trained patch calibration model comprises: determining multiple sets of input data based on position information indicating positions of the plurality of patches in the imaging data; and determining and calibrating the one or more target patches by inputting the plurality of patches into the trained patch calibration model, respectively.

A further aspect of the present disclosure may relate to a calibration system. The calibration system comprising: at least one storage device storing a set of instructions; and at least one processor configured to communicate with the at least one storage device, wherein when executing the set of instructions, the at least one processor is configured to direct the system to: obtain imaging data; divide the imaging data into a plurality of patches; and calibrate the imaging data based on one or more target patches of the plurality of patches, wherein the one or more target patches is a part of the plurality of patches.

In some embodiments, wherein the one or more target patches include one or more abnormal points; and to calibrate the imaging data based on the one or more target patches of the plurality of patches comprises, the system is directed to: determine the one or more target patches by processing the plurality of patches using at least one trained first classification model; calibrate the imaging data by calibrating the one or more target patches.

In some embodiments, wherein the imaging data includes K-space data, to determine the one or more target patches by processing the plurality of patches using at least one trained first classification model, the system is directed to: generate a reconstructed image based on the K-space data; determine whether the reconstructed image includes artifacts; and determine the one or more target patches by processing the plurality of patches using the at least one trained first classification model based on a determination result of whether the reconstructed image includes artifacts.

In some embodiments, wherein to calibrate the imaging data by calibrating the one or more target patches, the system is directed to: obtain one or more calibrated target patches by calibrating the one or more target patches using a trained artifact calibration model; calibrate the imaging data based on the one or more calibrated target patches.

In some embodiments, wherein to determine the one or more target patches by processing the plurality of patches using the at least one trained first classification model, the system is directed to: determine multiple sets of input data based on position information indicating positions of the plurality of patches in the imaging data; and determine the one or more target patches by inputting the multiple sets of input data into the at least one trained first classification model, respectively.

In some embodiments, wherein to determine the one or more target patches by processing the plurality of patches using the at least one trained first classification model, the system is directed to: preprocess the plurality of patches; and determine the one or more target patches by processing the plurality of preprocessed patches using the at least one trained first classification model.

In some embodiments, wherein to calibrate the imaging data based on the one or more target patches of the plurality of patches, the system is directed to: calibrate the imaging data by inputting the plurality of patches into a trained patch calibration model, wherein the trained patch calibration model is configured to determine and calibrate the one or more target patches.

A further aspect of the present disclosure may relate to a non-transitory computer-readable storage medium. The non-transitory computer readable medium comprising instructions that, when executed by at least one processor, direct the at least processor to perform a calibration method, the calibration method comprising: obtaining imaging data; dividing the imaging data into a plurality of patches; and calibrating the imaging data based on one or more target patches of the plurality of patches, wherein the one or more target patches is a part of the plurality of patches.

A further aspect of the present disclosure may relate to a method for magnetic resonance imaging. The method for magnetic resonance imaging may include obtaining imaging data; determining one or more target patches including abnormal point(s) in the imaging data, wherein the one or more target patches are part of imaging data; calibrating the imaging data based on the one or more target patches including the abnormal point(s).

In some embodiments, the determining the one or more target patches including the abnormal point(s) in the imaging data may include dividing the imaging data into a plurality of patches according to a first preset parameter; obtaining the one or more target patches including the abnormal point(s) by inputting the plurality of patches into a trained first classification model.

In some embodiments, the imaging data may include K-space data. The method may further include: obtaining a reconstruction image corresponding to the K-space data; determining whether the reconstruction image includes artifacts; determining whether the K-space data include abnormal point(s) according to a judgment result of the reconstruction image.

In some embodiments, wherein the determining whether the reconstruction image includes artifacts may include: segmenting at least one image block according to a second preset parameter; determining whether the reconstruction image includes artifacts by using a trained second classification model based on the at least one image block.

In some embodiments, the calibrating the imaging data based on the one or more target patches including the abnormal point(s) may include: determining position information of the abnormal point(s); performing artifact calibration on one or more target patches including the abnormal point(s) based on the position information to obtaining one or more calibrated target patches; updating the imaging data based on the one or more calibrated target patches.

In some embodiments, the determining the position information of the abnormal point(s) may include: for each abnormal point, determining a reference position of a patch that includes the abnormal point; determining a position of the abnormal point in the imaging data using a semantic segmentation neural network based on the reference position.

In some embodiments, the calibrating the imaging data based on the one or more target patches including the abnormal point(s) may include: obtaining one or more calibrated target patches by using a trained artifact calibration model to determine position information of the abnormal point(s); and performing the artifact calibration on the one or more target patches including the abnormal point(s) based on the position information.

In some embodiments, the method for magnetic resonance imaging may further include: generating a magnetic resonance image based on the calibrated imaging data, wherein sparking artifacts in the calibrated imaging data may be suppressed or eliminated.

A further aspect of the present disclosure may relate to a system for magnetic resonance imaging. The system may include an obtaining module configured to obtain imaging data; a detection module configured to determine one or more target patches including abnormal point(s) in the imaging data, wherein the one or more target patches are part of imaging data; a calibration module configured to calibrate the imaging data based on the one or more target patches including the abnormal point(s).

A still further aspect of the present disclosure may relate to a non-transitory computer readable medium. The non-transitory computer readable medium may include executable instructions that, when executed by at least one processor, cause the at least one processor to effectuate a method comprising: obtaining imaging data; determining one or more target patches including abnormal point(s) in the imaging data, wherein the one or more target patches are part of imaging data; calibrating the imaging data based on the one or more target patches including the abnormal point(s).

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
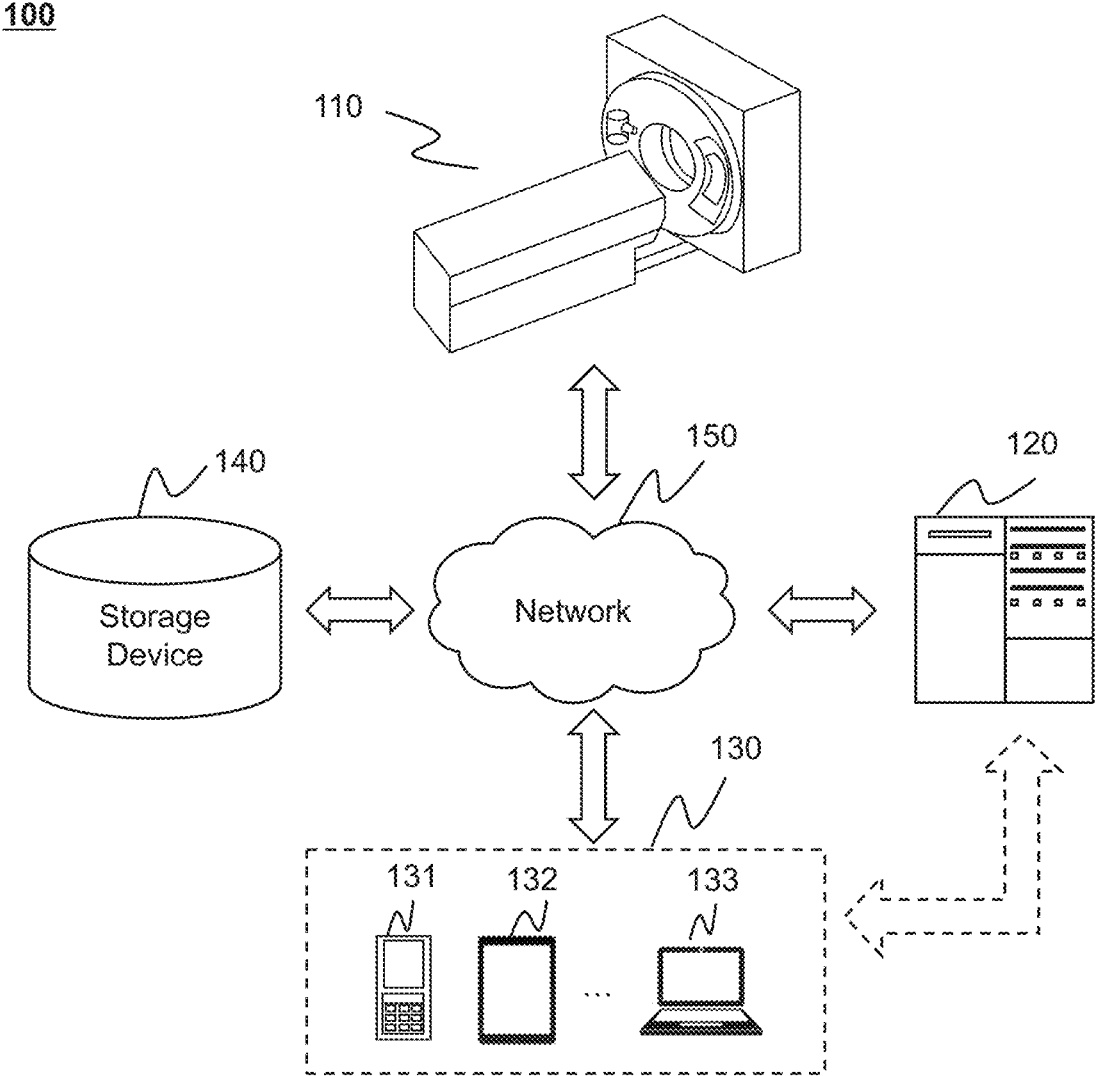
FIG. 1 is a schematic diagram illustrating an exemplary application scenario of a calibration system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," or "block," as used herein, refers to logic embodied in hardware or firmware, or to a collection of software instructions. A module or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Electrically Programmable Read-Only-Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It may be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The function and method of operation of these and other features, characteristics, and related structural elements of the present application, as well as component combinations and manufacturing economy, may become more apparent from the following description of the accompanying drawings, which constitute part of the specification of this application. It should be understood, however, that the drawings are for purposes of illustration and description only and are not intended to limit the scope of the present disclosure. It should be understood that the drawings are not to scale.

The terminology used herein is to describe particular example embodiments only and is not intended to be limiting. As used herein, the singular forms "a," "an," and "the" may be intended to include the plural forms as well, unless the context indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

The flowchart is used in this specification to illustrate the operations performed by the system according to the embodiment of the present disclosure, and the relevant description is to help better understand the magnetic resonance imaging method and/or system. It should be understood that the preceding or following operations are not necessarily performed in the exact order. Instead, the various steps can be processed in reverse order or simultaneously. At the same time, other actions can be added to these procedures, or a step or steps can be removed from these procedures.

The term "image" in the present disclosure is used to collectively refer to image data (e.g., scan data, projection data) and/or images of various forms, including a two-dimensional (2D) image, a three-dimensional (3D) image, a four-dimensional (4D) image, etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image (e.g., a second image, or a first image, etc.) and really exist in or on the subject's body. The term "region," "position," and "region" in the present disclosure may refer to a position of an anatomical structure shown in the image or an actual position of the anatomical structure existing in or on the subject's body, since the image may indicate the actual position of a certain anatomical structure existing in or on the subject's body. The terms "organ" and "tissue" are used interchangeably referring to a portion of a subject.

In MRI scanning, due to system faults or external interferences (e.g., RF noises caused by excessive electromagnetic emissions from devices other than MR scanners), sparking artifacts may exist in MRI images collected by an MRI device. Sparking artifacts may generally appear as alternating bright and dark bands in clinical images (e.g., as shown in an image in the image field on the right side of the straight line in FIG. 4) and as random spots with abnormally large intensities in K-space data (as shown as a bright pixel in an image in the K-space on the left side of the straight line in FIG. 4), which may affect doctors' diagnosis. Common system faults may include poor contact of electronic switches or other components during sampling by a high-speed ADC, a wire tip discharge; and common external interferences may include an RF signal crosstalk of a wireless transmitting device.

The occurrence of sparking artifacts is often difficult to predict in advance. When an image with sparking artifacts is collected in clinical scanning of a patient, the patient often needs to be rescanned. However, the rescanning not only increases the time and equipment cost, but also is not suitable for some special scenarios (e.g., a critically ill patient, contrast-enhanced MRI where a patient is injected with drugs to enhance the scan and thus cannot be rescanned immediately, etc.). In some embodiments, the sparking artifacts in the image may be automatically detected and calibrated by conventional algorithms, such as a thresholding algorithm and/or an iterative filtering algorithm. However, it is difficult to determine a suitable threshold, and the conventional algorithms are prone to misjudgment for areas where the magnitudes of the spark artifacts are close to those of the real signals (for example, a central area of the K-space).

The embodiments of the present disclosure disclose a calibration method for medical imaging. The method may include dividing imaging data into a plurality of patches, inputting the plurality of patches into at least one trained first classification model to obtained patches including abnormal points. (i.e., target patches), and calibrating the imaging data based on the patches including abnormal points. Through dividing the imaging data and performing the detection of the abnormal points on the plurality of divided patches, whether the imaging data includes the abnormal points and a rough position of the abnormal points in the imaging data (e.g., the K-space) may be determined. Further, calibrating the patches including the abnormal points, rather than calibrating the original imaging data, may reduce the amount of data processing and improve the calibration efficiency. By using the calibration method provided in the present disclosure, the imaging data may be calibrated automatically in the imaging process, the accuracy and efficiency of calibration may be improved, the time cost may be saved, and a secondary injury to patients caused by rescanning may be avoided. In some embodiments, because abnormal points at different positions in imaging data have different characteristics and effects, different calibration strategies may be carried out for patches at different positions based on position information of the patches to improve the calibration accuracy. For example, different preprocessing parameters, different trained first classification models, or different pre-set thresholds (which are used to determine whether a patch is a target patch including abnormal point(s)) may be used for a position in a center area of K-space and a position in an edge area of K-space.

FIG. 1 is a schematic diagram illustrating an exemplary application scenario of a calibration system according to some embodiments of the present disclosure.

As shown in FIG. 1, in some embodiments, a calibration system 100 may include an imaging device 110, a processing device 120, a terminal 130, a storage device 140, and network 150. In some embodiments, various components of the calibration system 100 may be connected to each other through the network 150 or directly without the network 150. For example, the imaging device 110 and the terminal 130 may be connected through the network 150. As another example, the imaging device 110 and the processing device 120 may be connected or directly connected through the network 150. As a further example, the imaging device 120 and the terminal 130 may be connected or directly connected through the network 150.

The imaging device 110 may be used to scan a target object (or a portion thereof) located in its detection area and collect image data related to the target object or the portion thereof. In some embodiments, the target object may be biological or abiotic. For example, the target object may include a patient, an artificial object, or the like. In some embodiments, the target object may include a specific part of a body, such as a head, a chest, an abdomen, etc., or any combination thereof. In some embodiments, the target object may include specific organs, such as a heart, an esophagus, a trachea, a bronchus, a stomach, a gallbladder, a small intestine, a colon, a bladder, a ureter, a uterus, a fallopian tube, etc., or any combination thereof. In some embodiments, the target object may include an area of interest (ROI), such as a tumor, a nodule, or the like.

In some embodiments, the imaging device 110 may include an X-ray device, a computed tomography imaging device (CT), a three-dimensional (3D) CT, a four-dimensional (4D) CT, an ultrasonic imaging component, a fluoroscopy imaging component, a nuclear MRI device, a single-photon emission computed tomography (SPECT) device Positron emission tomography (PET) equipment, etc. For example purposes, the present disclosure takes the MRI device as an example, which is not intended to limit the scope of the present discourse.

In some embodiments, the imaging device 110 may be an MRI device. In some embodiments, the MRI device may include a magnet assembly, a gradient coil assembly, and an RF assembly.

The magnet assembly may generate a first magnetic field (also be referred to as a main magnetic field) for polarizing the target object. For example, the magnet assembly may include a permanent magnet, a super conductive magnet, a resistance electromagnet, or the like.

The gradient coil assembly may generate a second magnetic field (also be referred to as a gradient magnetic field). For example, the gradient coil assembly may include an X gradient coil, a Y gradient coil, and a Z gradient coil. The gradient coil assembly may generate one or more magnetic field gradient pulses for the main magnetic field in an X direction (Gx), a Y direction (Gy), and a Z direction (Gz) to encode space information of the scanning object. In some embodiments, the X direction may be designated as a frequency encoding direction and the Y direction may be designated as a phase encoding direction. In some embodiments, Gx may be used for frequency encoding or signal readout, which may be commonly referred to as a frequency encoding gradient or a readout gradient. In some embodiments, Gy may be used for phase encoding, commonly referred to as a phase encoding gradient. In some embodiments, Gz may be used for slice selection to obtain two-dimensional K-space data. In some embodiments, Gz may be used for phase encoding to obtain three-dimensional K-space data.

The RF coil assembly may include one or more RF transmitting coils and/or one or more RF receiving coils. The RF transmitting coil(s) may transmit RF pulses to the target object. Under a synergistic action of the main magnetic field/gradient magnetic field and the RF pulse, a magnetic resonance signal related to the target object may be generated according to the pulse sequence. The RF receiving coil(s) may obtain the magnetic resonance signal from the object. A transformation operation (e.g., Fourier transformation) may be used to process the magnetic resonance signal to fill the K-space and obtain the K-space data.

The processing device 120 may process data and/or information obtained from the imaging device 110, the terminal 130, and/or the storage device 140. For example, the processing device 120 may process the K-space data detected by the imaging device 110 to obtain calibrated K-space data. As another example, the processing device 120 may generate one or more machine learning models for medical imaging data calibration. In some embodiments, the processing device 120 may be a single server or a group of servers. The group of servers may be centralized or distributed. In some embodiments, the processing device 120 may be local or remote. For example, the processing device 120 may access information and/or the data from the imaging device 110, the terminal 130, and/or the storage device 140 through the network 150. As another example, the processing device 120 may be directly connected to the imaging device 110, the terminal 130, and/or the storage device 140 to access information and/or data. In some embodiments, the processing device 120 may be implemented on a cloud platform. For example, the cloud platform may include a private cloud, a public cloud, a hybrid cloud, a community cloud, a distributed cloud, an inter-cloud cloud, a multi-cloud, or any combination thereof.

The terminal 130 may include a mobile device 131, a tablet computer 132, a notebook computer 133, etc., or any combination thereof. In some embodiments, the terminal 130 may interact with other components in the calibration system 100 through the network 150. For example, the terminal 130 may transmit one or more control instructions to the imaging device 110 through the network 150 to control the imaging device 110 to scan the target object according to the instructions. For another example, the terminal 130 may also receive an MRI image generated by the processing device 120 through the network 150 and display the MRI image for analysis and confirmation by an operator. In some embodiments, the mobile device 131 may include a smart home device, a wearable device, a mobile device, a virtual reality device, an augmented reality device, or any combination thereof.

In some embodiments, the terminal 130 may be part of the processing device 120. In some embodiments, the terminal 130 may be integrated into the processing device 120 as a console of the imaging device 110. For example, a user (e.g., a doctor or a nurse) of the calibration system 100 may control the imaging device 110 through the console, such as direct the imaging device 110 to scan the target object, etc.

The storage device 140 may store data (e.g., K-space data of the target object, a reconstructed image, etc.), instructions, and/or any other information. In some embodiments, the storage device 140 may store data collected from the imaging device 110, the processing device 120, and/or the terminal 130. For example, the storage device 140 may store K-space data and a reconstructed image of the target object collected from the imaging device 110, etc. In some embodiments, the storage device 140 may store data and/or instructions that the processing device 120 may execute or use to perform the exemplary methods described in the present disclosure.

In some embodiments, the storage device 140 may include a combination of one or more of a mass memory, a removable memory, a volatile read-write memory, a read-only memory (ROM), etc. In some embodiments, the storage device 140 may be implemented through a cloud platform described in the present disclosure.

In some embodiments, the storage device 140 may connect to the network 150 to communicate with the one or more components (e.g., the processing device 120, the terminal 130) of the calibration system 100. The one or more components of the calibration system 100 may read data or instructions in the storage device 140 through the network 150. In some embodiments, the storage device 140 may be part of the processing device 120 or be independent and directly or indirectly connected to the processing device 120.

The network 150 may include any suitable network capable of facilitating the exchange of information and/or data in the calibration system 100. In some embodiments, the one or more components of the calibration system 100 (e.g., the imaging device 110, the processing device 120, the terminal 130, the storage device 140) may exchange information and/or data with the one or more other components of the calibration system 100 through the network 150. For example, the processing device 120 may obtain imaging data of the target object from the imaging device 110 through the network 150. In some embodiments, the network 150 may include a public network (e.g., the Internet), a private network (e.g., a local area network (LAN), a wide area network (WAN)), a wired network (e.g., Ethernet), a wireless network (e.g., an 802.11 network, a wireless Wi Fi network, etc.), a cellular network (e.g., a long-term evolution (LTE) network), a frame relay network, a Virtual private network (VPN), a satellite network, a telephone network, a router, a hub, a server computer, etc. In some embodiments, the network 150 may include one or more network access points. For example, the network 150 may include wired and/or wireless network access points, such as base stations and/or Internet switching points, through which the one or more components of the calibration system 100 may connect to the network 150 to exchange data and/or information.

It should be noted that the above description is merely provided for the purposes of illustration, and not intended to limit the scope of the present disclosure. For persons having ordinary skills in the art, multiple variations and modifications may be made under the teachings of the present disclosure. The features, structures, methods, and other features of the exemplary embodiments described in the present disclosure may be combined in various ways to obtain additional and/or alternative exemplary embodiments. For example, the calibration system 100 may also include a display device for outputting and displaying a magnetic resonance image generated by the processing device 120. However, those variations and modifications do not depart from the scope of the present disclosure.

Figure 2:
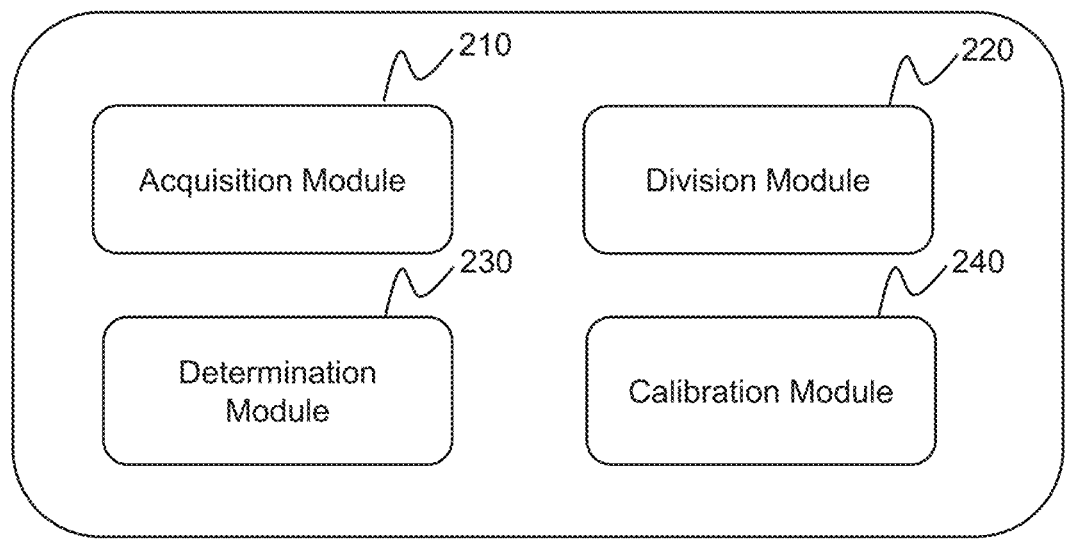
FIG. 2 is a block diagram illustrating an exemplary processing device according to some embodiments of the present disclosure.

FIG. 2 is a block diagram illustrating an exemplary processing device according to some embodiments of the present disclosure.

As shown in FIG. 2, in some embodiments, the processing device 120 may include an acquisition module 210, a division module 220, a determination module 230, and a calibration module 240. In some embodiments, one or more modules of the processing device 120 may be connected to each other, and the connection may be wireless and/or wired.

The acquisition module 210 may be configured to obtain imaging data. In some embodiments, the imaging data may include K-space data of a target object.

The division module 220 may be configured to divide the imaging data into a plurality of patches. In some embodiments, the division module 220 may divide the imaging data into the plurality of patches according to a first preset parameter.

The determination module 230 may be configured to determine one or more target patches by processing the plurality of patches. In some embodiments, the target patch(es) may include one or more patches including one or more abnormal points. In some embodiments, the determination module 230 may determine the target patch(es) by processing the plurality of patches using at least one trained first classification model. In some embodiments, a trained first classification model may determine whether a patch is a target patch by encoding the position information of the patch.

The calibration module 240 may be configured to calibrate the imaging data based on one or more target patches of the plurality of patches, wherein the one or more target patches is a part of the plurality of patches. In some embodiments, the calibration module 240 may determine the position information of the one or more abnormal points in the target patch(es), and calibrate the target patch(es) based on the position information of the one or more abnormal points to obtain the calibrated target patch(es). In some embodiments, the calibration module 240 may determine position information of the abnormal points using an abnormal point segmentation model. In some embodiments, the calibration module 240 may calibrate the target patch(es) using a trained artifact calibration model to obtain the calibrated target patch(es). In some embodiments, the calibration module 240 may update the imaging data based on the calibrated target patch(es) to obtain the calibrated imaging data. In some embodiments, the calibration module 240 may input the plurality of patches into a trained patch calibration model to calibrate the imaging data.

The description of the processing device 120 is illustrative, and not intended to limit the scope of the present disclosure. For persons having ordinary skills in the art, multiple variations and modifications may be made under the teachings of the present disclosure. However, those variations and modifications do not depart from the scope of the present disclosure. For example, the one or more modules of the above processing device 120 may be omitted or integrated into a single module. As another example, the processing device 120 may include one or more additional modules, such as a storage module for data storage, or the like.

Figure 3:
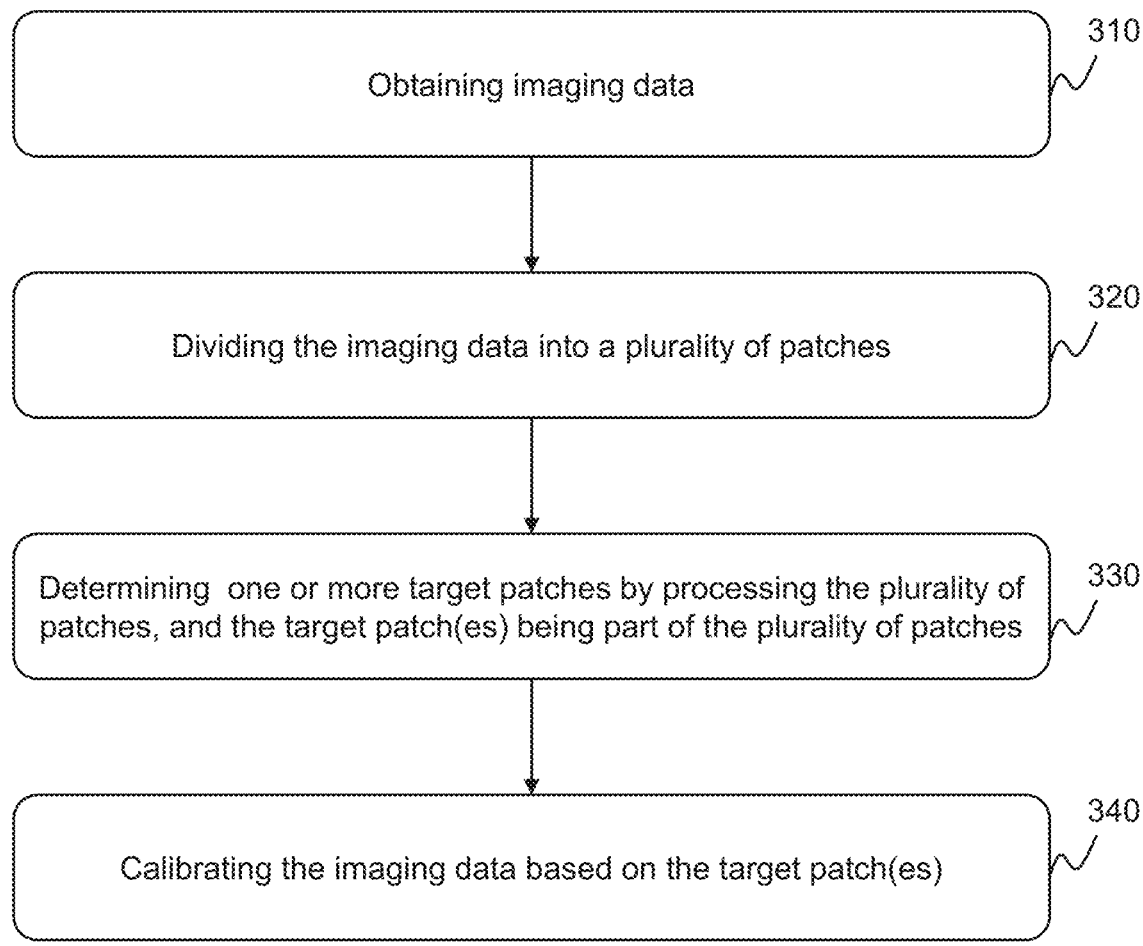
FIG. 3 is a flowchart illustrating an exemplary calibration method according to some embodiments of the present disclosure.

FIG. 3 is a flowchart illustrating an exemplary calibration method according to some embodiments of the present disclosure.

In some embodiments, process 300 may be performed by the calibration system 100. For example, the process 300 may be implemented as an instruction (e.g., an application program) and stored in a storage device (e.g., the storage device 140 or an external storage device of the calibration system 100). The processing device 120 (e.g., the one or more modules shown in FIG. 2) may execute instructions, and when executing instructions, the processing device 120 may be configured to execute the process 300. The process 300 presented below may be illustrative. In some embodiments, the process 300 may be accomplished with one or more additional operations not described and/or without one or more operations described below. In addition, the operation sequence of the process 300 shown in FIG. 3 and described below is not intended to be limiting.

In 310, the processing device 120 may obtain imaging data. In some embodiments, operation 310 may be performed by the acquisition module 210.

The imaging data may include data to be calibrated, such as K-space data with bright spots, artifacts, white spots, etc.

In some embodiments, the imaging data may include K-space data of a target object. Normally, images may generally have two forms: images in the pixel domain (the image domain) and images in the frequency domain, and these two forms may be converted into each other by Fourier transformation and inverse Fourier transformation. Fourier transformation may be a transformation from the pixel domain to the frequency domain, and inverse Fourier transformation may be a transformation from the frequency domain to the pixel domain. The K-space may refer to a space for storing information of the frequency domain. Merely by way of example, in the imaging process, an MRI device may use three gradients and RF pulses to perform a space encoding (a slice selection, a frequency encoding, and a phase encoding) on MRI signals. The collected analog echo signals including space information may be converted into digital signals and filled into the K-space to obtain the K-space data. An inverse Fourier transformation may be performed on the K-space data to obtain an image of the target object (i.e., a pixel domain image).

Figure 4:
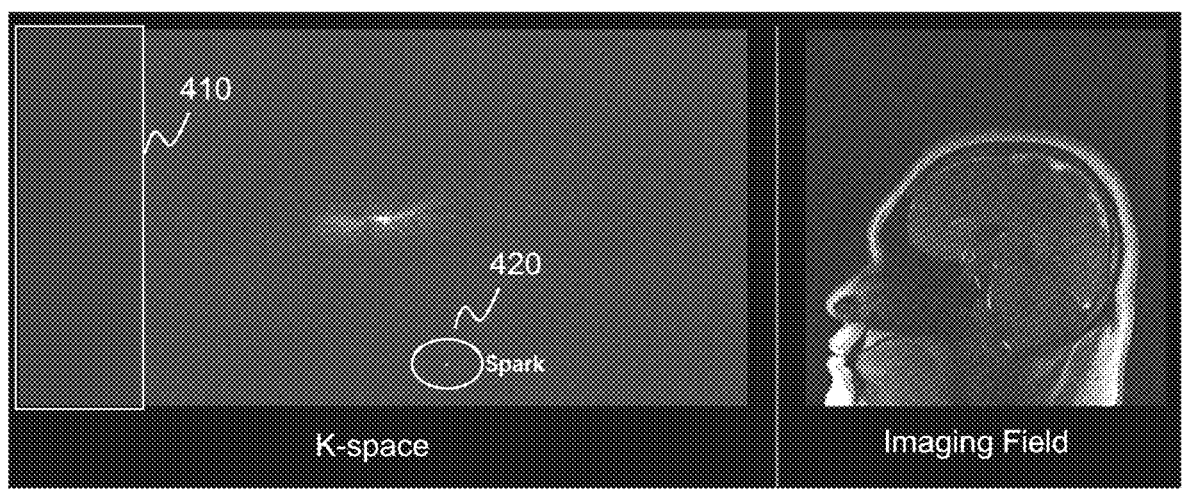
FIG. 4 is a schematic diagram illustrating exemplary imaging data according to some embodiments of the present disclosure.

In the K-space, different frequencies and phases may represent different space positions, and the amplitude may represent MR signal strength. For example, the left side of the straight line in FIG. 4 shows the K-space data, and the right side shows an image in the image domain corresponding to the K-space data. In some embodiments, the K-space data may include 2D K-space data or 3D K-space data. For example, the 3D K-space data may be represented in a three-dimensional coordinate system, which may include three coordinate axes corresponding to the slice selection, the frequency encoding, and the phase encoding. The 2D K-space data may be represented in a two-dimensional coordinate system, which may include two coordinate axes corresponding to two of the slice selection, the frequency encoding, and the phase encoding. In some embodiments, the K-space data may include full sampling K-space data or under-sampling K-space data. For example, the K-space data shown on the left side of the straight line in FIG. 4 is an under-sampling image, and a white frame 410 may correspond to the uncollected K-space data.

In some embodiments, the imaging data may include a pixel domain image of the target object, for example, a reconstructed image. In some embodiments, the processing device 120 may obtain the imaging data from the imaging device. For example, the processing device 120 may instruct the imaging device 110 to scan the target object to generate the K-space data. In some embodiments, the processing device 120 may obtain the imaging data from a storage device such as the storage device 140. In some embodiments, the processing device 120 may obtain the K-space data as the imaging data by performing Fourier transformation on an MRI image of the target object.

In 320, the processing device 120 may divide the imaging data into a plurality of patches. In some embodiments, operation 320 may be performed by the division module 220.

In some embodiments, the plurality of patches may have a same size and shape. In some embodiments, the data included in the plurality of patches may be different from each other. In some embodiments, the plurality of patches may not overlap with each other. In some embodiments, there may be an overlap between at least part of patches.

In some embodiments, the processing device 120 may divide the imaging data into the plurality of patches according to a first preset parameter. In some embodiments, the first preset parameter may be related to a size (e.g., a length, a width, a diameter, a perimeter, etc.) of the patches, a shape (e.g., a square, a rectangle, a polygon, a circle, etc.) of the patches, or the like. For example, the K-space data of 426*1024 may be divided into 448 patches with a size of 32*32 according to a size parameter of 32*32.

In some embodiments, the first preset parameter may be determined according to at least one of the dimensions of the imaging data, the collection manner of the imaging data, and the arrangement of data points of the imaging data, or the like. Merely by way of example, when the imaging data is one-dimensional linear data (such as 1*N), each patch may be a line segment of a certain length (such as 1*M, M<N); when the imaging data is two-dimensional data (such as N*N), each patch may be a rectangle (such as M*M, M<N); when the imaging data is three-dimensional data (such as N*N*N), each patch may be a three-dimensional cube (such as M*M*M, M<N).

In some embodiments, the first preset parameter may be determined according to the data type of the imaging data (e.g., the K-space data). For example, the size of the patches may be determined to be 32*32 according to a size of the K-space corresponding to the MRI imaging device. In some embodiments, the first preset parameter may be determined according to a clinical scanning parameter. In some embodiments, the processing device 120 may adjust the first preset parameter in real time according to an actual situation, for example, different first preset parameters may be set according to the different scenes of different scans. In some embodiments, the processing device 120 may automatically set or adjust the first preset parameter. For example, the processing device 120 may automatically determine or adjust the first preset parameter in real time according to information of the target object, statistic information of big data, a setting habit of medical staff, etc.

Figure 6:
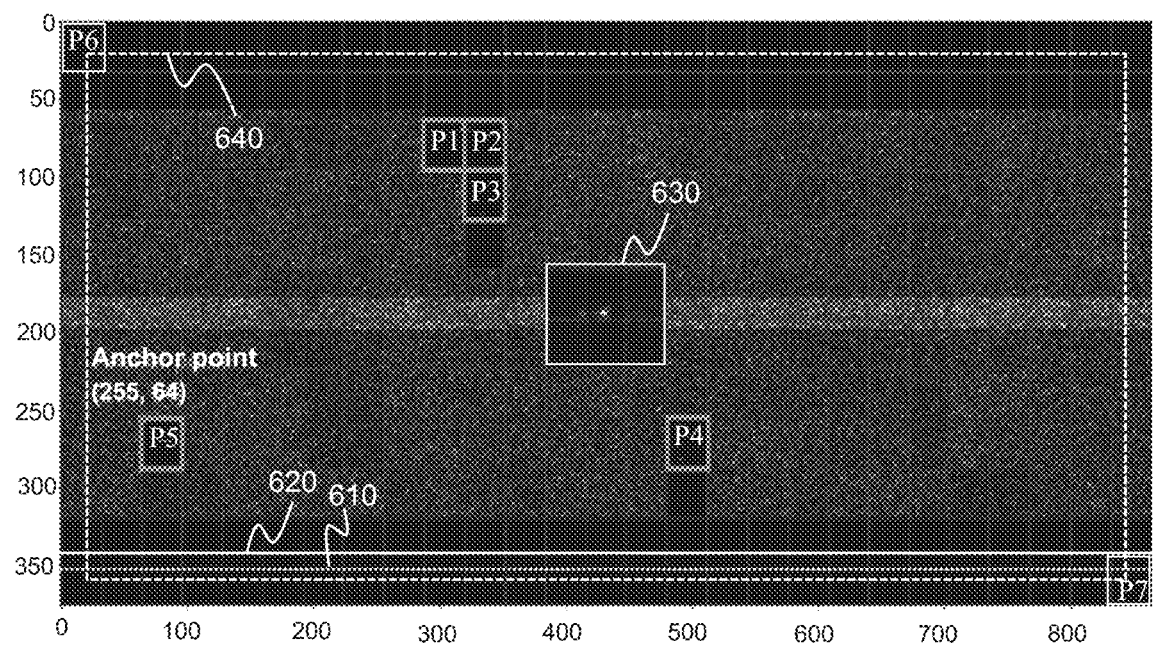
FIG. 6 is a schematic diagram illustrating exemplary imaging data according to some embodiments of the present disclosure.

In some embodiments, the plurality of patches may be equal in size to each other. For example, as shown in FIG. 6, when the K-space data of 426*1024 is divided according to a first preset parameter of 32*32, because 426 is not an integer multiple of 32, the side length of the patches corresponding to a last row obtained after dividing the K-space data may be smaller than 32. In such cases, the plurality of patches with equal size may be obtained by moving up the cropping position for the last row of the patches. For example, a white virtual line 610 in FIG. 6 may be moved to a position of a white real line 620 in the FIG. 6. In some embodiments, at least two of the plurality of patches may overlap. For example, a part including a spark bright spot in the K-space data may be divided into multiple patches including all or part of this spark bright spot. As another example, as shown in FIG. 6, there may be an overlap between the patches corresponding to the last row of the K-space data and the patches corresponding to a penultimate row of the K-space data.

In 330, the processing device 120 may determine one or more target patches by processing the plurality of patches, and the target patch(es) may be part of the plurality of patches. In some embodiments, operation 330 may be performed by the determination module 230.

In some embodiments, the target patch(es) may include one or more patches including one or more abnormal points. A difference between a pixel value of an abnormal point and a preset standard value (such as a statistical average pixel value of an image without abnormal points or artifacts) or a pixel value of other pixel points (such as more than 80% of a pixel point in the image) may exceed a specific threshold. For example, the abnormal point(s) may include a strip line in the imaging data, a bright spot in the imaging data, a ring artifact in the imaging data, a white spot in the imaging data, a black spot in the imaging data, etc. Merely by way of example, in MRI scanning, due to the external interferences or the system faults, artifacts may exist in MRI images obtained by an MRI device, which may be shown as random bright spots in the K-space data. Common system faults may include poor contact of electronic switches or other components during sampling by the high-speed ADC, the wire tip discharge; and common external interferences may include instantaneous RF signal crosstalk of the wireless transmitting device. For example, as shown in FIG. 4, there may be a spark/bright spot (as shown in a white circle 420) in the K-space data obtained by the MRI imaging device due to the occurrence of system faults, and there may be artifacts like alternating bright and dark bands in the image domain image (the right side of the straight line) corresponding to the K-space data.

In some embodiment, the processing device 120 may determine the target patch(es) by processing the plurality of patches using at least one trained first classification model.

In some embodiments, the processing device 120 may preprocess the plurality of patches. The processing device 120 may further determine the target patch(es) by processing the preprocessed patches using the at least one trained first classification model. In some embodiments, the preprocessing may include an image normalization, a subsection process of pixel points, or the like. For example, for each patch, the processing device 120 may perform image normalization on the patch according to a preprocessing parameter, and convert the patch into a patch including pixels values within a normalized range (e.g., pixel values between 0 and 1, or pixel values with zero mean and unit variations). Merely by way of example, if using Max-Min normalization, for each patch, the processing device 120 may convert each point in the patch with a pixel value equal or larger than the Max intensity to 1 and a pixel value equal or less than the Min intensity to 0, and any pixel value in between to 0 to 1. A preprocessed patch with normalized intensity range will be obtained after this Max-Min normalization process. In some embodiments, each patch may correspond to the same preprocessing parameter. For example, the processing device 120 may preprocess each patch separately based on the same normalization methods and parameters.

In some embodiments, the preprocessing methods and parameters may be predetermined according to an impact degree of the abnormal points on the imaging data. For example, historical K-space data collected in historical imaging processes and/or historical calibration processes may be analyzed. If a spark point of the historical K-space data does not cause artifacts in the corresponding reconstructed image, it may be determined as a low-impact abnormal point; if a spark point of the historical K-space data causes artifacts in the corresponding reconstructed image, but the artifacts are not serious (if it does not impact disease diagnosis), it may be determined as an impact abnormal point; if a spark point of the historical K-space data causes artifacts in the corresponding reconstructed image and impact disease diagnosis, it may be determined as a high-impact abnormal point. Further, the processing device 120 may determine three pixel threshold values according to the magnitudes of the low-impact abnormal points, the impact abnormal points, and the high-impact abnormal points of the historical K-space data, respectively. The three threshold values (i.e., the Max value in Max-Min normalization) may include a first threshold value, a second threshold value, a third threshold value, wherein the third threshold value is greater than the second threshold value, and the second threshold value is greater than the first threshold value. The processing device 120 may preprocess the patches based on the three thresholds values. For example, for a patch, the processing device 120 may apply different preprocessing methods and parameters based on the location of the patch and the type of sparks need to be detected.

In some embodiments, the preprocessing methods and parameters corresponding to different patches may be different. Merely by way of example, for each patch, the processing device 120 may determine the preprocessing parameter of Max-Min normalization of the patch according to the position information of the patch in the imaging data (e.g., the K-space data). For example, the smaller the distance between the patch and the center point of the K-space, the larger Max value will be applied for the Max-Min normalization of the patch. Merely by way of example, for a patch located in the central area of the K-space, the Max value for the Max-Min normalization may be twice the preset standard value (i.e., the adaptive standard value can be chosen as the intensity of K-space center. When the pixel value of a pixel in the patch is equal or larger than Max value, which is equal or larger than twice the standard value, set the normalized value of the pixel to 1). For a patch located in the edge area of the K-space, the Max-value for the Max-Min normalization may be 0.1 times the preset standard value (for example, when the pixel value of a pixel in the patch is equal or larger than the Max value, which is equal or larger than 0.1 times preset standard value, set the normalized value of the pixel to 1). The center area of the K-space may refer to a sub-region whose distance to a central point of the K-space is less than a first distance threshold, for example, the area shown by a white solid line rectangular frame 630 in the middle of FIG. 6. The edge area may be an area other than the central area in the K-space or an area whose distance to an edge of the K-space is less than a second distance threshold. In some embodiments, the preset standard value may be adaptive based on the input data, include the K-space center, root-of-squares of the intensities of K-space center area (e.g., 5*5 area of the K-space center), or an average value of the pixel points of the imaging data without artifacts or abnormal points.

The intensity values of the abnormal points in different areas of the K-space may be different. Generally, an intensity value of a point located in the center area of the K-space may be higher than an intensity value of a point in the edge area, and the point located in the center area may be easily misjudged as an abnormal point. Based on the position information of the patches in the imaging data, different preprocessing parameters may be used for patches at different positions to enhance the contrast between the pixels in each patch. In particular, for patch(es) located in the central area of K-space, selecting a larger Max value for Max-Min normalization may enhance an intensity contrast between the abnormal points in the central area of the K-space and real signal points having intensities close to the abnormal points (such as a central point of the K-space or a point near the central point of the K-space). This may avoid misjudging a center point having the intensities close to the abnormal points and/or real signal points near the center point as the abnormal points during abnormal point detection and improve the judgment accuracy and calibration accuracy of the abnormal points. On the other hand, setting different preprocessing parameters (e.g., Max value for Max-Min normalization) for the central area and the edge area of the K-space may reduce the number of abnormal points identified in the central area without impacting the calibration effect, which, in turn, reduces the analysis of some abnormal points located in the center area of the K-space that have little impact on image quality, and reduces the amount of data analysis and improve the calibration efficiency.

In some embodiments, the preprocessing operation of the patches may be omitted, and the processing device 120 may directly determine the target patch(es) based on the at least one trained first classification model and the original patches. For illustration purposes, the following describes how to determine the target patch(es) based on the trained first classification model and the Max-Min normalized patches with fixed parameters.

In some embodiments, a trained first classification model may refer to a trained model for detecting whether a patch or the imaging data includes abnormal points. In some embodiments, the trained first classification model may include a deep learning model, such as a convolutional neural network (CNN), a vision transformer (VIT) deep learning model, or the like. In some embodiments, one of the CNN model or the VIT deep learning model may be selected as the trained first classification model according to the real-time situation. For example, the selection may be performed based on the imaging data (such as whether the intensity contrast between different pixel points in the imaging data is obvious or not), the accuracies of the CNN model and the VIT deep learning model. The accuracies of the CNN model and the VIT deep learning model may be determined based on historical calibrations performed using these two models. For example, if an intensity variance between different pixel points in the imaging data exceeds a certain threshold, the CNN model may be selected as the final first classification model. If the intensity variance between different pixel points is less than the certain threshold, the VIT deep learning model may be selected as the final first classification model.

In some embodiments, an input of the trained first classification model may include a patch, and an output may be a probability that the patch includes abnormal points or whether the patch includes abnormal points. For example, the plurality of the patches may be input into the trained first classification model at the same time or separately, and the trained first classification model may output the probability that each patch includes abnormal points, such as a probability value between 0 and 1. As another example, the plurality of the patches may be input into the trained first classification model at the same time or separately, and the trained first classification model may output a judgment result of whether each patch includes abnormal points, for example, 0 means not included and 1 means included.

In some embodiments, the trained first classification model may output a probability value that a patch includes abnormal points, the processing device 120 may determine whether the patch includes abnormal points based on a preset threshold (i.e., a preset classification threshold). For example, the preset threshold may be set to 0.5. If the probability value that the patch includes abnormal points is greater than 0.5, the patch may be deemed as including abnormal points and determined as a target patch. If the probability value that the patch includes abnormal points is less than 0.5, the patch may be not deemed as including abnormal points. In some embodiment, the trained first classification model may determine whether the patch is a target patch (i.e., determine whether the patch includes abnormal points) based on the preset classification threshold. In some embodiments, the preset classification threshold may be determined automatically or manually. For example, a medical staff may manually adjust the preset classification threshold according to requirements for image quality. As another example, the processing device 120 may automatically determine the preset classification threshold based on the historically setting values of the preset classification threshold, user feedback information regarding a recognition result, or the like.

In some embodiments, the preset thresholds (i.e., the preset classification thresholds) corresponding to different patches may be the same or different. Merely by way of example, since abnormal points at different positions have different impacts on image quality, the processing device 120 may determine the corresponding preset classification threshold according to the position information of the patches in the imaging data. For example, bright spots located in the central area of the K-space may generally have less impact on image quality than bright spots located in other areas of the K-space. At the same time, because pixels in the central area of the K-space are brighter than other parts, a patch including bright spots in this area is easily misidentified as a target patch (i.e., a patch including abnormal points). Therefore, the preset classification threshold value corresponding to a patch located in the central area of the K-space may be set to be greater than the preset classification threshold value corresponding to a patch located in other areas of the K-space. In such cases, compared with patches in other areas, a patch located in the K-space may be determined as the target patch by the trained first classification model only if it has a greater probability of including abnormal points. This may avoid situations where a real signal point in the central area is incorrectly identified as an abnormal point because the intensities of the real signal point is greater than other parts, and affect the accuracy of the abnormal point identification. In some embodiments, patch(es) located in the central area of the K-space may be deemed as not including abnormal points and omitted from subsequent processing.

In some embodiments, the target patch(es) may be determined based on the position information of the plurality of patches in the imaging data using at least one trained first classification model. The position information of a patch may include a coordinate position of the patch (e.g., a coordinate of a central point of the patch) in the K-space data, etc. For example, different preset classification thresholds may be set for patches in different locations. In some embodiments, the position information of the patches may be input into a judgment layer of a trained first classification model to determine the target patch(es). The judgment layer may be used to determine whether a patch including abnormal points (for example, determine whether the probability of the patch including abnormal points is greater than the corresponding preset threshold) based on encoded data (such as a vector) output by other structural layers of the trained first classification model (such as a convolution layer, a pooling layer, etc.). For example, the judgment layer may be a full connection layer of the trained first classification model.

In some embodiments, a trained first classification model may determine whether a patch is a target patch by encoding the position information of the patch, i.e., the output result of the trained first classification model may be generated by analyzing the position information of the patch. For example, if the trained first classification model is the CNN model, a position encoding component may be added into the fully connected layer of the CNN model. The position encoding component may be used to analyze the position information of the patch, so that the CNN model may determine a final output result based on the position information. As another example, when the trained first classification model is the VIT deep learning model, the encoding of position information may be realized based on a transformer architecture of the VIT deep learning model. For example, when training the VIT deep learning model, a labeled patch and location position information of the labeled patch may be used as input data, and the VIT deep learning model may learn a relationship between the position information of the labeled patch and the probability that the labeled patch is a target patch including abnormal points. Merely by way of example, the VIT deep learning model may include a linear projection of flattened patches embedding layer and a transformer encoder layer. After one or more patches are input into the VIT deep learning model, a plurality of vectors may be obtained through the linear projection of flattened patches embedding layer, wherein the plurality of vectors may be combined with position tokens. Then the patch vectors with both patch information and position information may be input into the transformer encoder layer, and the transformer encoder layer may output the same number of hidden vectors as the number of patches. Finally, the hidden vectors corresponding to a patch or more patches may be input to a Multilayer Perceptron (MLP) Head for predicting whether the patch(es) are target patch(es).

In some embodiments, the at least one trained first classification model may include a plurality of trained first classification models corresponding to different positions in the K-space. For each patch in the plurality of patches, a corresponding first classification model may be determined from the plurality of trained first classification models according to the position information of the patch, and the selected first classification model may be used to determine whether the patch is the target patch. For example, in model training, a trained first classification model M1 may be trained for patches located in the central area of the K-space, and a trained first classification model M2 may be trained for patches located in other areas of the K-space. For a specific patch, one of the M1 and M2 may be selected as the first classification model according to the position information of the specific patch in the K-space, and the patch may be input into the corresponding first classification model to determine whether the patch is the target patch.

In some embodiments, whether a patch located in the center area of the K-space includes abnormal points (i.e. whether it is the target patch) may be determined separately from other patches (for example, the patch located in the center area of the K-space may be input into the trained first classification model M1 while other patches may be input into the trained first classification model M2). Alternatively, it may be a default setting to assume that a patch of the center area of the K-space does not include abnormal points). Alternatively, patches in the center area and other areas of the K-space may be analyzed together using a single trained first classification model. For example, the six patches in the white solid-line rectangular frame 630 in the center of FIG. 6 may be deemed as not including abnormal points by default, or the six patches may be processed by the first classification model M1, or the preset classification threshold of the six patches may be adjusted, etc. This may avoid misjudging a center point having the intensity close to the abnormal points and/or real signal points near the center point as an abnormal point during abnormal point detection. In this way, the center point with intensity near that of the abnormal point may be avoided misjudging as an abnormal point, which can improve the accuracy of the detection of the abnormal point.

In some embodiments, multiple sets of input data may be determined based on the position information of the plurality of patches in the imaging data, and the multiple sets of input data may be respectively input into the at least one trained first classification model to determine the target patch(es). In some embodiments, two or more patches that are positionally related may be determined to be in the same set of the input data. For example, two or more adjacent patches in the K-space (e.g., the patches P1, P2, P3 in FIG. 6) may be considered as patches that are positionally related. As another example, patches located at two conjugate symmetrical positions in the K-space (e.g., an upper left patch P6 and a lower right patch P7 in FIG. 6) may be considered as patches that are positionally related. As a further example, patches located in the same circle in the K-space (for example, the patches passed by a dotted rectangular box 640 in FIG. 6) may be considered as patches that are positionally related.

By determining the multiple sets of input data based on the position correlation of the patches and determining the target patch(es) for each set of input data respectively, the conjugate symmetry and the neighborhood similarity of the K-space may be fully used in the recognition of the target patch(s), which can improve the recognition accuracy and efficiency of the target patch(s).

In some embodiments, a trained first classification model may be generated by the processing device 120 or another processing device (such as a processing device of a supplier of the first classification model) based on the labeled patch. Merely by way of example, the processing device may obtain sample K-space data including spark artifacts through simulation based on large amounts of historical clinical data (such as adding simulated spark spots into the retrospective spark-free K-space data or simulated spark-free K-space data). Alternatively, the processing device 120 may obtain K-space data including abnormal points collected during historical imaging as sample K-space data. Further, the processing device 120 may divide the sample K-space data into the plurality of labeled patches according to the first preset parameter. The processing device 120 may then determine whether each labeled patch includes abnormal points (such as spark bright spots), and the determination result may be used as a label of the labeled patch. The processing device 120 may obtain the trained first classification model by inputting the labeled patch and the label of the labeled patch into the initial deep learning model for training. In some embodiments, the first classification model may be trained in any suitable way, which is not limited in the present disclosure.

In some embodiments, the processing device 120 may generate different trained first classification models for different positions in the K-space. For example, the first classification model M1 may be trained for patches in the central area of the K-space. In some embodiments, the same trained first classification model may be generated for different positions in the K-space. For example, labeled patches in the central area and labeled patches in the other areas may be mixed and used together in the process of training the first classification model. For the labeled patches in the central area of the K-space, the corresponding preset classification thresholds may be adjusted, such as letting the preset classification thresholds greater than the preset classification threshold corresponding to the labeled patches located in other areas of the K-space. In this way, the preset classification thresholds may be set for pixels at different positions according to the different impact degrees of these pixels on the reconstructed image. For example, the intensities of a pixel point located in the central area of the K-space needs to be much greater than the preset standard value to cause artifacts in the reconstructed image, while the intensities of a pixel point located in the edge area of the K-space only needs to be slightly greater than the preset standard value to cause artifacts in the reconstructed image. This may also avoid misjudging a real signal point in the central area of the K-space having the intensities close to abnormal points as an abnormal point, which can improve the accuracy of the abnormal point detection. As another example, when generating the trained first classification model, labeled patches located in the central area of the K-space may be marked to improve the recognition ability of the trained first classification model with respect to such patches. As a further example, when the training datas are obtained by simulation, different amplitudes may be simulated for spark points at different positions in the K-space, so that the intensities of the spark points closer to the center of the K-space may be greater, which may enhance the contrast between the spark points and other pixel points located in the central area.

In some embodiments, the processing device 120 may obtain a reconstructed image corresponding to the K-space data and determine whether the reconstructed image includes artifacts. According to the determination result of whether the reconstructed image includes artifacts, the processing device 120 may further adjust the thresholds (i.e., the preset classification thresholds) for determining whether the patches of the K-space data include abnormal points.

In some embodiments, the reconstructed image corresponding to the K-space data may be obtained by performing inverse Fourier transformation. For example, if the K-space is fully sampled, the K-space data may be directly reconstructed into the image domain through inverse Fourier transformation to obtain the corresponding reconstructed image. As shown in FIG. 4, if the K-space data are undersampled, i.e., part of the K-space (e.g., an area in the white rectangular box 410 in FIG. 4) is not sampled, the conjugate symmetry of the K-space may be used to fill the un-sampled part with the collected data in another part that has conjugate symmetry with the un-sampled part. Then, the data of the remaining un-sampled part after filling may be filled with 0, and the complete K-space data after filling may be reconstructed into the corresponding reconstructed image in the image domain through the inverse Fourier transformation.

In some embodiments, the processing device 120 may crop at least one image block from the reconstructed image according to a second preset parameter. Further, the processing device 120 may determine whether the reconstructed image includes artifacts by processing the at least one image block using a trained second classification model.

In some embodiments, the second preset parameter may be related to the shape of the image block(s), the size of the image block(s), etc. In some embodiments, the second preset parameter and the first preset parameter may be the same or different. In some embodiments, the second preset parameter may have any reasonable value, such as 224*224, etc. In some embodiments, the second preset parameter may be determined based on at least one of an image domain parameter (such as, a resolution of the reconstructed image, a size of the reconstructed image, etc.), and an image standard size, etc. In some embodiments, the processing device 120 may automatically determine the second preset parameter. In some embodiments, the second preset parameter may be set manually by the user. For example, the user may manually set the second preset parameter through the terminal 130.

In some embodiments, the trained second classification model may refer to a model for detecting whether an image block or the reconstructed image includes artifacts. In some embodiments, the trained second classification model may include a deep learning model, such as a convolutional neural network or a VIT deep learning model. In some embodiments, an input of the trained second classification model may include an image block, and an output of the trained second classification model may be a judgment result of whether the image block includes artifacts or the probability that the image block includes artifacts. For example, the cropped image block may be input into the trained second classification model, and the trained second classification model may output the judgment result of whether the image block includes the artifacts. For example, 0 may denote not included, 1 may denote included.

Figure 5:
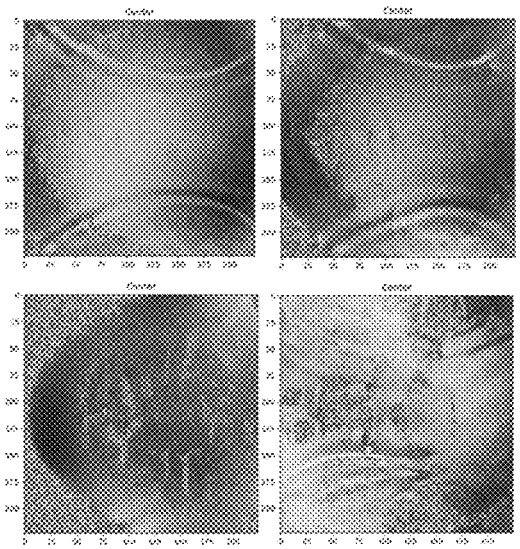
FIG. 5 is a schematic diagram illustrating exemplary reconstructed images according to some other embodiments of the present disclosure.
Figure 5:
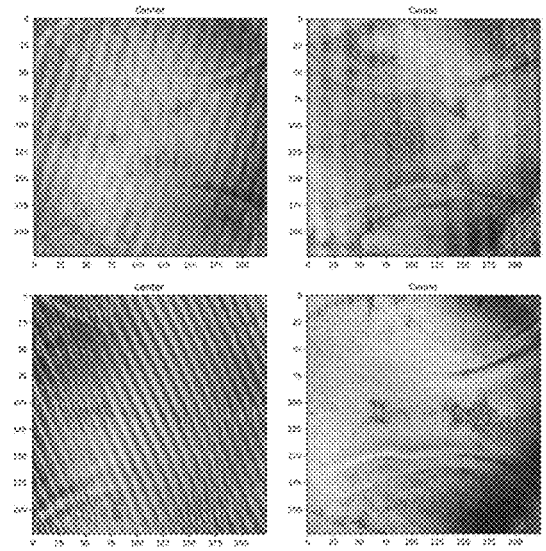

In some embodiments, the trained second classification model may be obtained by the processing device 120 or other processing device (e.g., the processing device of a supplier of the trained second classification model) based on one or more labeled image blocks. In some embodiments, a label used for training the second classification model may indicate whether a labeled image block includes artifacts. As shown in FIG. 5, a label 0 may indicate that a labeled image block includes no artifact, and label 1 may indicate that a labeled image block includes artifacts. The training process of the second classification model may be similar to the training process of the first classification model(s), and more descriptions may refer to the relevant description of the trained first classification model(s), which may not be repeated here.

In some embodiments, when the reconstructed image includes artifacts, the processing device 120 may determine that the K-space data includes abnormal points. When the reconstructed image does not include artifacts, the processing device 120 may determine that the K-space data does not include abnormal points or target patches. In some embodiments, when it is determined that the K-space data does not include abnormal points or the target patches (i.e., patches containing abnormal points) based on the reconstruction image, operation 330 may not be performed.

In some embodiments, the processing device 120 may adjust the preset classification threshold corresponding to the K-space data according to the judgment result of whether the reconstructed image includes artifacts. For example, when the reconstructed image does not include artifacts, the processing device 120 may adaptively increase the preset classification threshold, for example, from 0.5 to 0.9. In some embodiments, the processing device 120 may use the at least one trained first classification model to determine the target patch(es) according to the judgment result of whether the reconstructed image includes artifacts. For example, based on the judgment result, the processing device 120 may adjust the preset classification threshold used in a judgment layer of the at least one trained first classification model, the labels of the labeled patches of the at least one trained first classification model, etc.

Different abnormal points (such as the intensities, the pixel locations, or the shapes) in the K-space data have different impacts on the reconstructed image. For example, if there are only a limited number of bright spots (e.g., one bright spot) with relatively small intensities in the K-space data, it may not cause the artifacts in the corresponding reconstructed image, i.e., it does not impact disease diagnosis. If there are a plurality of bright spots with relatively large intensities in the K-space data, there may be significant artifacts in the corresponding reconstructed image. By determining whether the K-space data includes abnormal points based on the judgment result of whether the reconstructed image includes artifacts, abnormal point(s) that have little impact on the reconstructed image (such as abnormal points that may not cause visible artifacts) can be effectively filtered, which reduces the processing load of the calibration, and improves the calibration efficiency.

In 340, the processing device 120 may calibrate the imaging data based on the target patch(es). In some embodiments, operation 340 may be performed by the calibration module 240.

In some embodiments, the processing device 120 may determine the position information of the one or more abnormal points in the target patch(es), and calibrate the target patch(es) based on the position information of the one or more abnormal points to obtain the calibrated target patch(es). Further, the processing apparatus 120 may calibrate the imaging data based on the one or more calibrated target data patches.

In some embodiments, for an abnormal point in a target patch, the processing device 120 may determine the position of the target patch in the imaging data, and the position of the target patch may be used as a reference position of the abnormal point. Further, the processing device 120 may determine a rough position of the abnormal point in the imaging data based on the reference position. For example, the position coordinate of the upper left pixel or center pixel of the target patch in the K-space may be determined as the position coordinate of the abnormal point in the K-space. Merely by way of example, as shown in FIG. 6, patches P1, P2, P3, P4, and P5 may be determined as target patches having abnormal points. Taking the target patch P5 as an example, the position coordinate of the upper left pixel of the target patch P5 in the K-space may be (256, 64). Further, the processing device 120 may determine the position of the target patch P5 in the K-space as the rough position of abnormal points included in the target patch P5 in the K space, for example, the rough position of the abnormal points included in the target patch P5 in the K space may be (256, 64).

Figure 7:
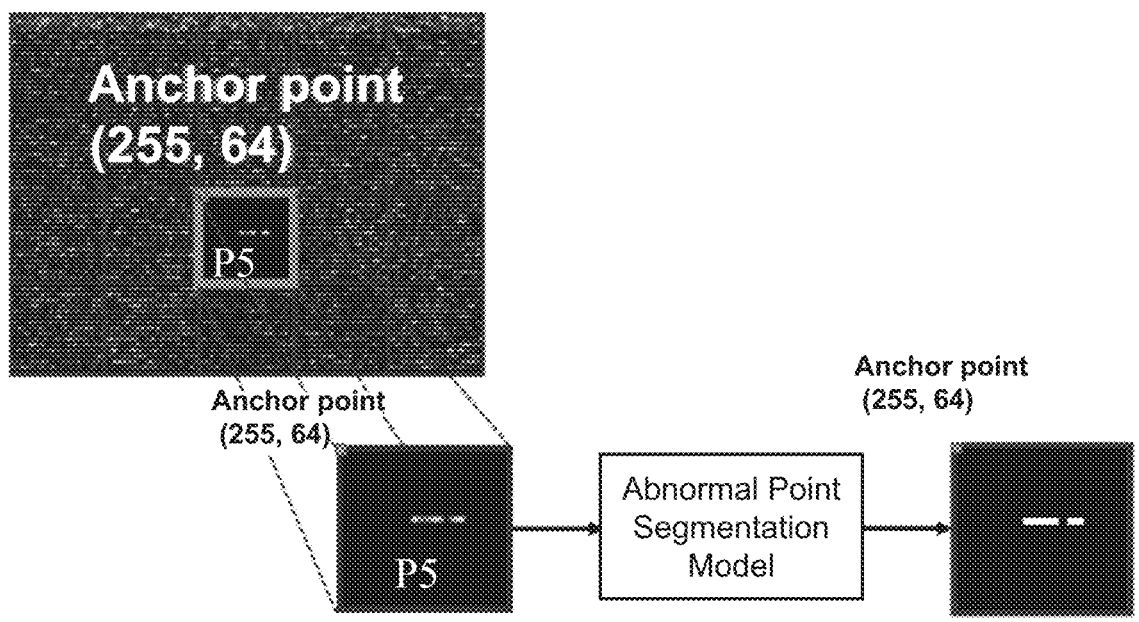
FIG. 7 is a schematic diagram illustrating an exemplary process of determining position information of abnormal points according to some embodiments of the present disclosure.

In some embodiments, the processing device 120 may determine position information of the abnormal points using an abnormal point segmentation model. For example, the abnormal point segmentation model may include a semantic segmentation neural network model, such as a U-Net, a SeeNet, a Deconv-NET, etc. In some embodiments, the processing device 120 may segment one or more abnormal points in the target patch(es) using the abnormal point segmentation model, and determine the position information of the abnormal point(s) in the target patch(es) based on the segmentation result. In some embodiments, the abnormal point segmentation model may be used to classify a pixel in an image into, for example, an abnormal point and a normal point. Merely by way of example, as shown in FIG. 7, the processing device 120 may input the target patch P5 in the K-space data into the abnormal point segmentation model. The abnormal point segmentation model may perform spark point segmentation on the target patch P5 to generate a 0/1 mask, wherein 0 in the mask may denote a normal point, and 1 in the mask may denote a spark point. The processing device 120 may determine the position coordinates of the spark points in the target patch P5 based on the mask.

In some embodiments, the abnormal point segmentation model may be obtained based on labeled target patches for training. For example, a label of the abnormal point segmentation model may include a 0/1 mask of the same size as the labeled target patch, wherein 0 in the mask may denote a normal point, and 1 in the mask may denote a spark point.

In some embodiments, the processing device 120 may determine the position information of an abnormal point in the imaging data based on the abnormal point segmentation model and the reference position of the abnormal point. The position information may reflect a precise coordinate of the abnormal point in the imaging data (such as the K-space data). Merely by way of example, as shown in FIGS. 6 and 7, the abnormal point segmentation model may take an upper left pixel of the target patch P5 as an anchor point. A coordinate $(pe_a, ro_a)$ of the anchor point may be determined as a rough position of each abnormal point of the target patch P5 in the K-space data, for example, $(pe_a, ro_a)=(256,64)$. A position coordinate (row, col) of each abnormal point in the target patch P5 may be determined using the abnormal point segmentation model. For example, when the coordinate of the anchor point is defined as (0, 0), the processing device 120 may determine that the positions of segmented abnormal points in the target patch P5 are [14, 14], [14, 15], [14, 16], [14, 18], [14, 19]. Finally, the processing device 120 may determine that the precise coordinate of each abnormal point in the K-space is $(pe_a+row, ro_a+col)$ based on the position coordinate of the anchor point in the K-space data and the position coordinate of the abnormal point in the target patch. Merely by way of example, if the position coordinate of an abnormal point in the target patch P5 is [14, 14], the exact coordinate of the abnormal point in the K-space may be (256+14, 64+14)=(270, 78).

In some embodiments, the processing device 120 may calibrate the target patch(es) based on the position of the target patch(es) to obtain the calibrated target patch(es). In some embodiments, the processing device 120 may calibrate the pixel value of a pixel point corresponding to each abnormal point by at least one of a filling method, an interpolation method, or a neural network-based value assignment method to obtain the calibrated target patch(es). The filling method may be used to fill the K-space data corresponding to the abnormal points to 0 or according to the conjugate symmetry of the K-space based on the collected data. For example, the processing device 120 may fill the K-space data corresponding to the abnormal points in the target patch(es) with 0 according to the position information of the abnormal points to obtain the calibrated target patch(es). In some embodiments, an interpolation method such as GeneRalized Autocalibrating Partial Parallel Acquisition (GRAPPA) may be used to interpolate the abnormal points based on the collected K-space data.

In some embodiments, the processing device 120 may calibrate the target patch(es) using a trained artifact calibration model to obtain the calibrated target patch(es). For example, through the trained artifact calibration model, the abnormal points in the target patch(es) may be segmented and the position information of the abnormal points may be determined at the same time, and the target patch(es) may be calibrated based on the position information to obtain the calibrated target patch(es). Through the trained artifact calibration model, abnormal points may be located and patch(es) including the abnormal points (i.e., the target patch(es)) may be calibrated at the same time. In some embodiments, the input of the trained artifact calibration model may include the target patch(es), and the output of the trained artifact calibration model may include the calibrated target patch(es). In some embodiments, the input of the trained artifact calibration model may include the target patch(es), and the output of the artifact calibration may include the calibrated imaging data. In some embodiments, the trained artifact calibration model may include a neural network including at least an encoder layer and a decoder layer, such as the U-Net network. In some embodiments, the trained artifact calibration model may be obtained by model training in any feasible way. For example, the trained artifact calibration model may be obtained based on a plurality of training datas including labeled patches with abnormal points and labeled patches without abnormal points, which may be not limited in the present disclosure.

In some embodiments, the processing device 120 may update the imaging data based on the calibrated target patch(es) to obtain the calibrated imaging data. For example, the processing device 120 may fill the calibrated target patch(es) to their corresponding position(s) in the K-space data. In some embodiments, the processing device 120 may calibrate the imaging data (such as the K-space data) based on the position information of the abnormal points to obtain the calibrated imaging data. For example, the processing device 120 may fill the abnormal points in the K-space data with 0 based on the position information of the abnormal points to obtain the calibrated imaging data. In some embodiments, the abnormal points in the calibrated imaging data, such as spark points, may be suppressed or eliminated.

Figure 12:
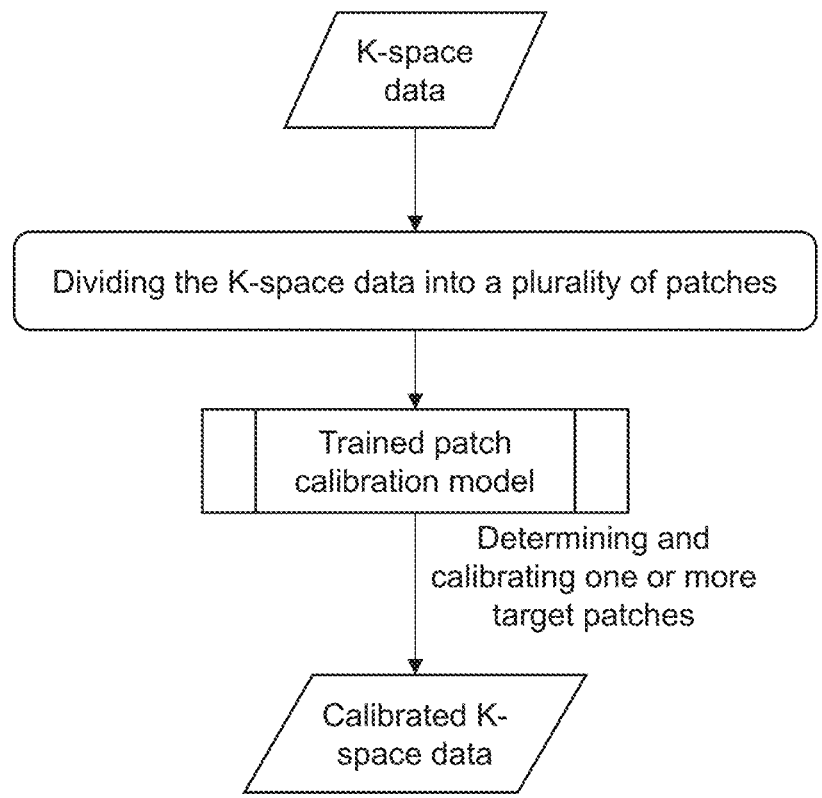
FIG. 12 is a schematic diagram illustrating an exemplary calibration method according to some other embodiments of the present disclosure.

In some embodiments, the processing device 120 may input the plurality of patches into a trained patch calibration model to calibrate the imaging data. The trained patch calibration model may be used to determine the target patch(es) and calibrate the target patch(es). For example, as shown in FIG. 12, the processing device 120 may divide the K-space data into the plurality of patches, and input the patches into the trained patch calibration model. The trained patch calibration model may implement the determination of the target patch(es) and the calibration of the target patch(es) at the same time, and output the calibrated target patch(es). Further, the processing device 120 may update the K-space data based on the calibrated target patch(es) to obtain the calibrated K-space data.

In some embodiments, the trained patch calibration model may update the imaging data based on the calibrated target patch(es) and output the calibrated imaging data. In some embodiments, the trained patch calibration model may calibrate the imaging data based on the position information of the one or more abnormal points and output the calibrated imaging data. In some embodiments, the processing device 120 may update the imaging data based on the calibrated target patch(es) output by the trained patch calibration model to obtain the calibrated imaging data.

In some embodiments, the trained patch calibration model may include a VIT deep learning model. In some embodiments, the trained patch calibration model may include a classification module and a calibration module. The classification module may be used to receive and analyze the one or more patches to determine the target patch(es). The calibration module may be used to calibrate the target patch(es) output by the classification module to obtain the calibrated target patch(es). For example, the trained patch calibration model may be a model having the network structure of a CNN model and a U-Net model (such as a model including an embedding layer, an encoding layer, a judgment layer, and a prediction layer). In some embodiments, the trained patch calibration model may be obtained by the processing device 120 or another processing device based on labeled training data. For example, the labeled training data of the trained patch calibration model may include one or more patch pairs each of which includes a labeled target patch and a corresponding calibrated labeled target patch.

By using the trained patch calibration model to simultaneously realize the judgment of whether a patch includes abnormal points and the calibration of target patches, the data processing load and processing operations may be reduced, the processing time may be saved, and the processing efficiency may be improved.

In some embodiments, a magnetic resonance image may be generated based on the calibrated imaging data. For example, based on the calibrated K-space data, a clinical image without sparking artifacts may be obtained for clinical diagnosis through image reconstruction and/or reprocessing.

It should be noted that the above-mentioned description of process 300 is for illustrative purposes only, and is not intended to limit the scope of the present disclosure. For those skilled in the art, without deviating from the principles of the present disclosure, various variations and modifications of the forms and the details of the above methods and systems may be made. However, these variations and modifications are also within the scope of the present disclosure. In some embodiments, one or more operations of process 300 may be omitted, and/or one or more additional operations may be added to process 300. For example, process 300 may include one or more additional operations for data calibration.

FIGS. 8-11 are schematic diagrams illustrating exemplary calibration methods according to some embodiments of the present disclosure.

Figure 8:
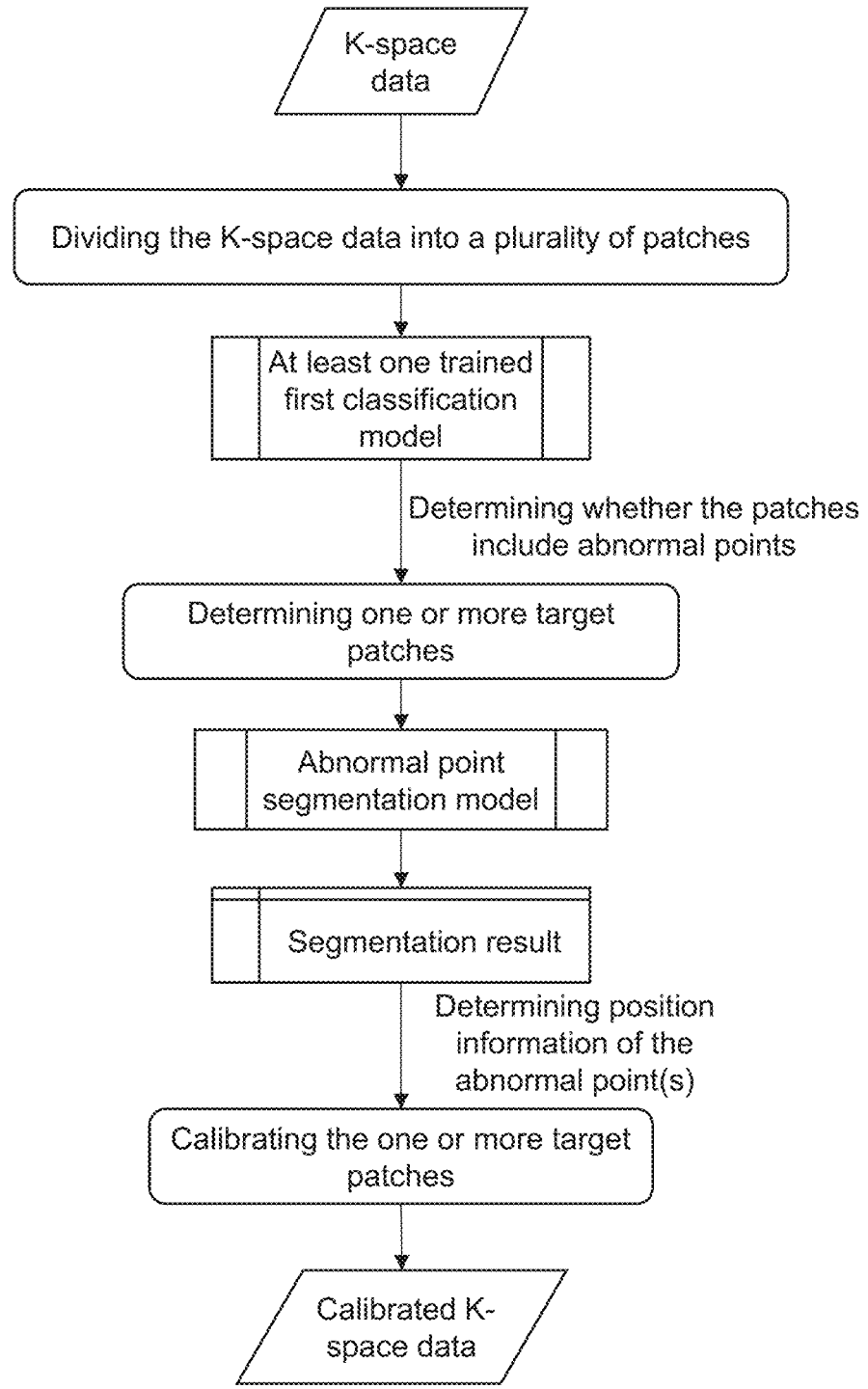
FIG. 8 is a schematic diagram illustrating an exemplary calibration method according to some embodiments of the present disclosure.

As shown in FIG. 8, in some embodiments, the processing device 120 may divide K-space data into a plurality of patches and input the plurality of patches into at least one trained first classification model separately or simultaneously. The at least one trained first classification model may output a judgment result of whether the patches include abnormal points. The processing device 120 may determine the target patch(es) based on the output of the at least one trained first classification model. Further, the processing device 120 may input the target patch(es) into an abnormal point segmentation model to segment one or more abnormal points in the target patch(es). The processing device 120 may determine the position information of the abnormal point(s) in the K-space data based on the segmentation result. The processing device 120 may calibrate the target patch(es) based on the position information to obtain the calibrated target patch(es). Further, the processing device 120 may update the K-space data based on the calibrated target patch(es) and output the calibrated K-space data.

Figure 9:
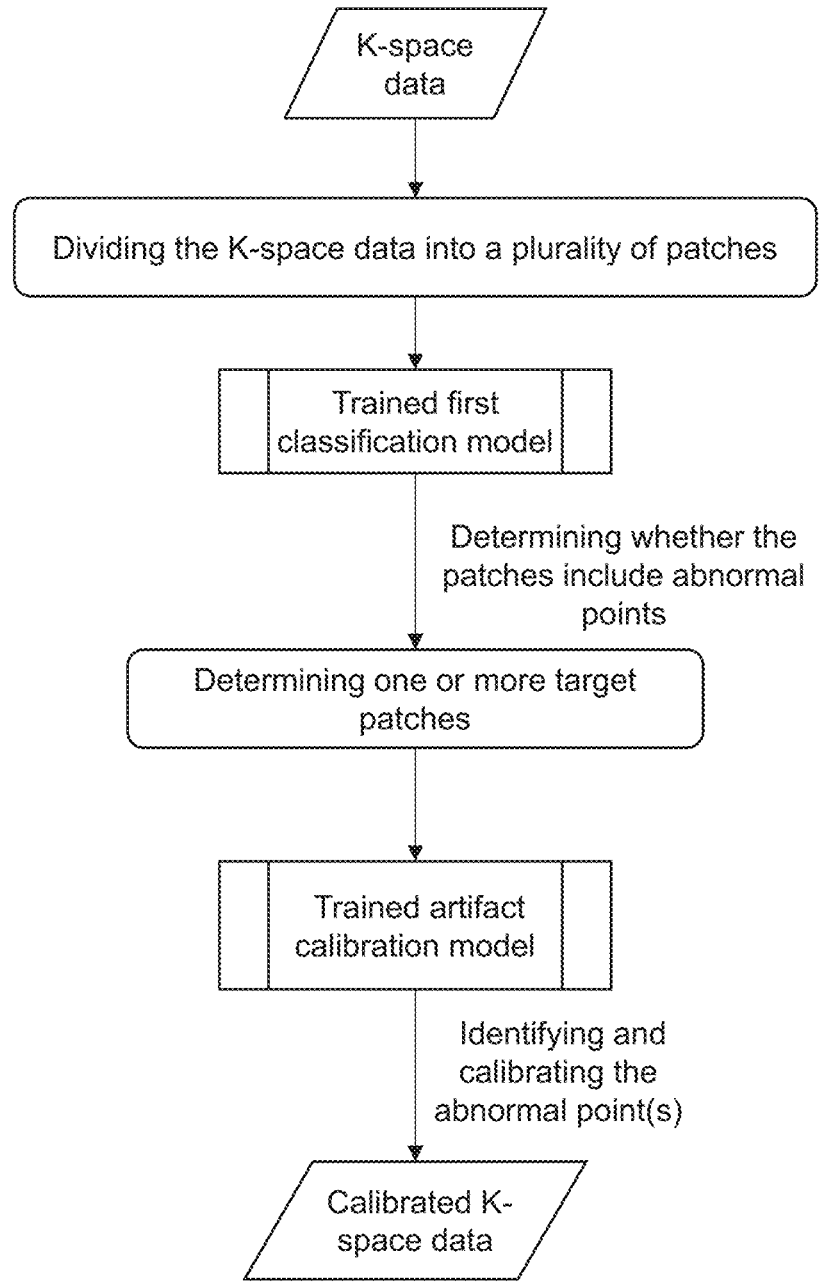
FIG. 9 is a schematic diagram illustrating an exemplary calibration method according to some other embodiments of the present disclosure.

As shown in FIG. 9, in some embodiments, the processing device 120 may divide K-space data into a plurality of patches and input the plurality of patches into at least one trained first classification model separately or simultaneously. The at least one trained first classification model may output a judgment result of whether the patches include abnormal points. The processing device 120 may determine the target patch(es) based on the output of the at least one trained first classification model. Further, the processing device 120 may input the target patch(es) into the trained artifact calibration model. The artifact calibration model may calibrate the target patch(es) (i.e., the artifact calibration model may simultaneously determine the position information of the abnormal point(s) in K-space data and calibrate the patches including abnormal points based on the position information) to obtain the calibrated target patch(es). The processing device 120 may update the K-space data based on the calibrated target patch(es), and output the calibrated K-space data finally.

Figure 10:
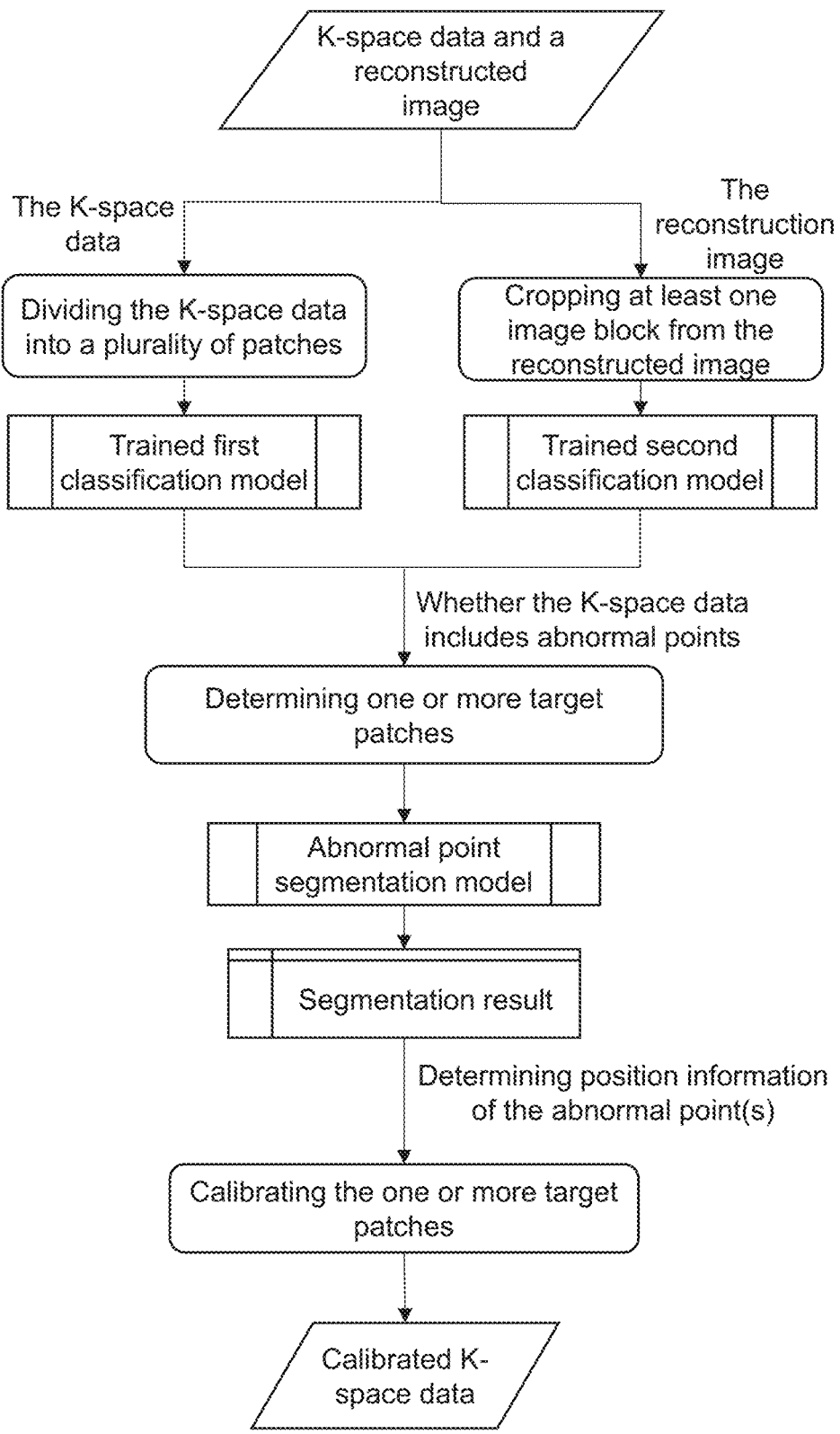
FIG. 10 is a schematic diagram illustrating an exemplary calibration method according to some other embodiments of the present disclosure.

As shown in FIG. 10, in some embodiments, the processing device 120 may crop at least one image block from a reconstructed image corresponding to K-space data and input the at least one image block into a trained second classification model. The trained second classification model may output a judgment result of whether the at least one image block includes artifacts. The processing device 120 may determine whether the reconstructed image includes artifacts based on the output of the trained second classification model. The processing device 120 may further determine whether the K-space data includes abnormal points based on the determination result of whether the reconstructed image includes artifacts. For example, the processing device 120 may determine that the K-space data includes abnormal points when the reconstructed image includes artifacts. Further, the processing device 120 may divide the K-space data into a plurality of patches and input the plurality of patches into at least one trained first classification model separately or simultaneously. The at least one trained first classification model may output a judgment result of whether the patches include abnormal points. Based on the output of the at least one trained first classification model, the processing device 120 may determine the target patch(es). Further, the processing device 120 may input the target patch(es) into an abnormal point segmentation model to segment one or more abnormal points in the target patch(es). The processing device 120 may calibrate the target patch(es) based on the position information to obtain the calibrated target patch(es). Further, the processing device 120 may update the K-space data based on the calibrated target patch(es) and output the calibrated K-space data finally. In some embodiments, when the reconstructed image does not include artifacts, the processing device 120 may adjust a preset threshold of the at least one trained first classification model, and then perform the subsequent data blocking (e.g., dividing the K-space data into a plurality of patches), the target patch determination, and the target patch calibration.

Figure 11:
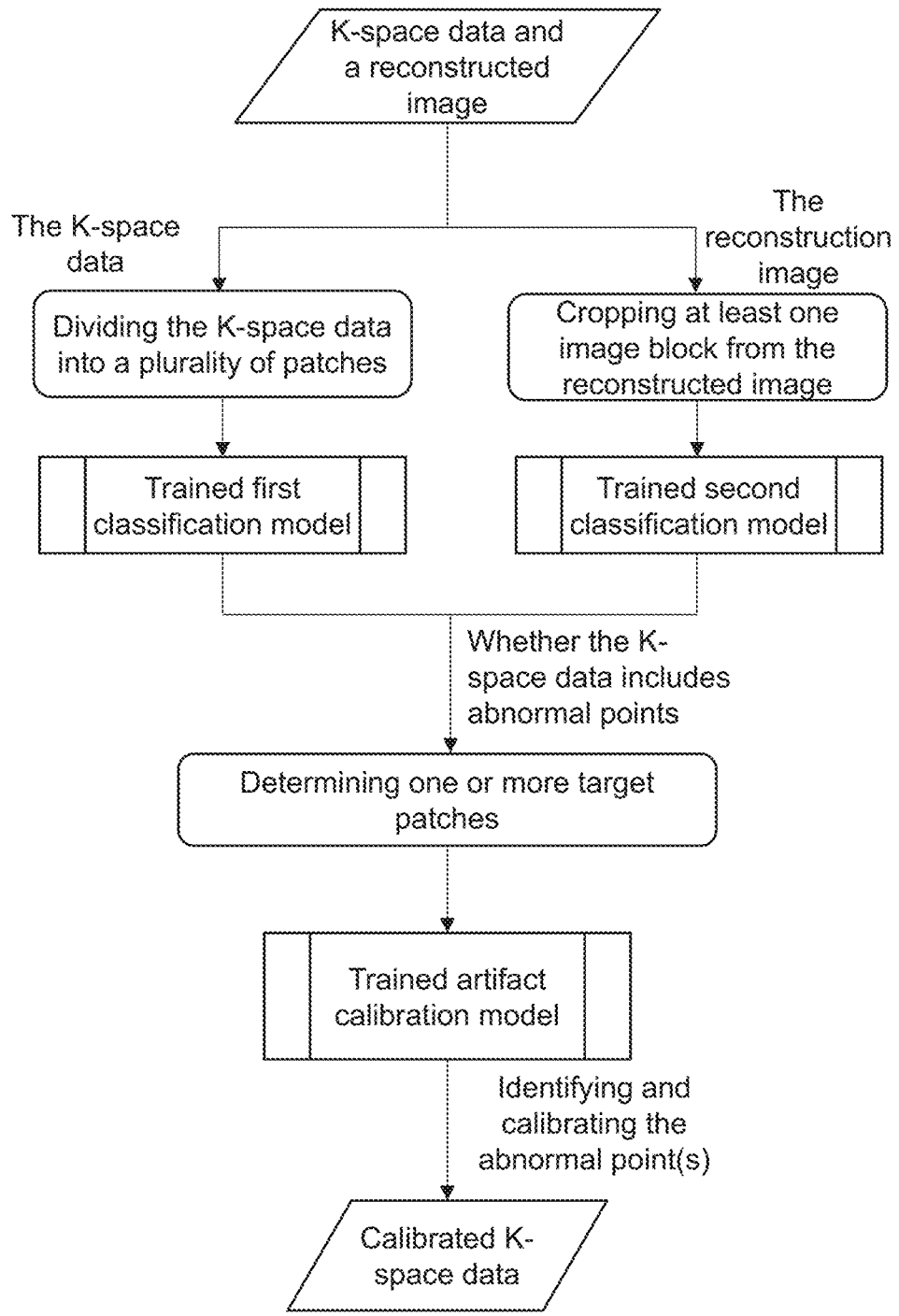
FIG. 11 is a schematic diagram illustrating an exemplary calibration method according to some other embodiments of the present disclosure.

As shown in FIG. 11, in some embodiments, the processing device 120 may crop at least one image block from a reconstructed image corresponding to K-space data and input the at least one image block into a trained second classification model. The trained second classification model may output a judgment result of whether the image block includes artifacts. The processing device 120 may determine whether the reconstructed image includes artifacts based on the output of the trained second classification model. The processing device 120 may further determine whether the K-space data includes abnormal points based on the determination result of whether the reconstructed image includes artifacts. For example, when the reconstructed image includes artifacts, the processing device 120 may determine that the K-space data includes abnormal points. Further, the processing device 120 may divide the K-space data into the plurality of patches and input the plurality of patches into the at least one trained first classification model separately or simultaneously. The at least one trained first classification model may output a judgment result of whether the patches include abnormal points. The processing device 120 may determine the target patch(es) based on the output of the at least one trained first classification model. Further, the processing device 120 may input the target patch(es) into the trained artifact calibration model. The trained artifact calibration model may calibrate the target patch(es) (i.e., the trained artifact calibration model may simultaneously determine the position information of the abnormal points in K-space data and calibrate the target patch(es) based on the position information), and output the calibrated target patch(es). The processing device 120 may update the K-space data based on the calibrated target patch(es), and output the calibrated K-space data finally. In some embodiments, when the reconstructed image does not include artifacts, the processing device 120 may adjust the preset threshold of the at least one trained first classification model, and then perform the subsequent data blocking, the target patch determination, and the target patch calibration.

Figure 13:
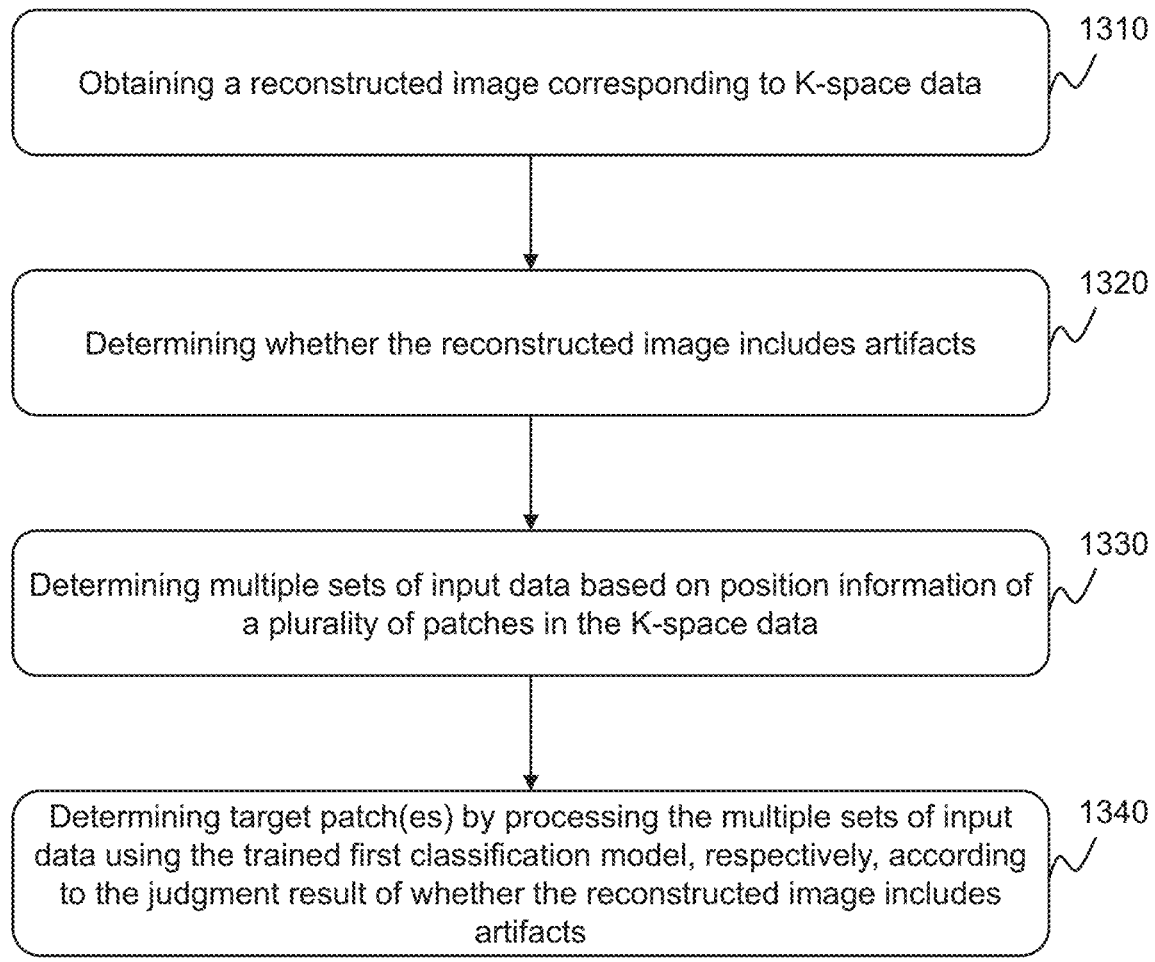
FIG. 13 is a schematic diagram illustrating an exemplary process of determining one or more target patches according to some embodiments of the present disclosure.
Figure 14:
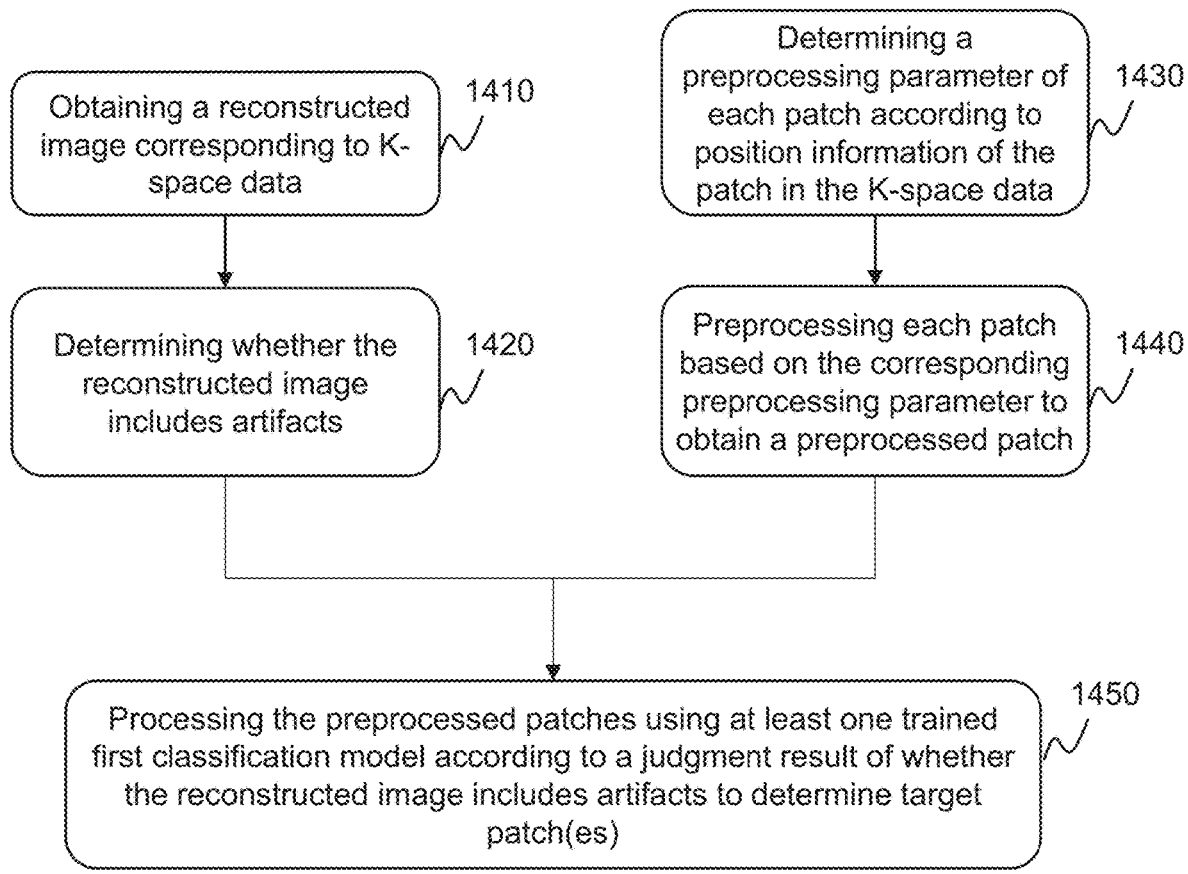
FIG. 14 is a schematic diagram illustrating an exemplary process of determining one or more target patches according to some other embodiments of the present disclosure.
Figure 15:
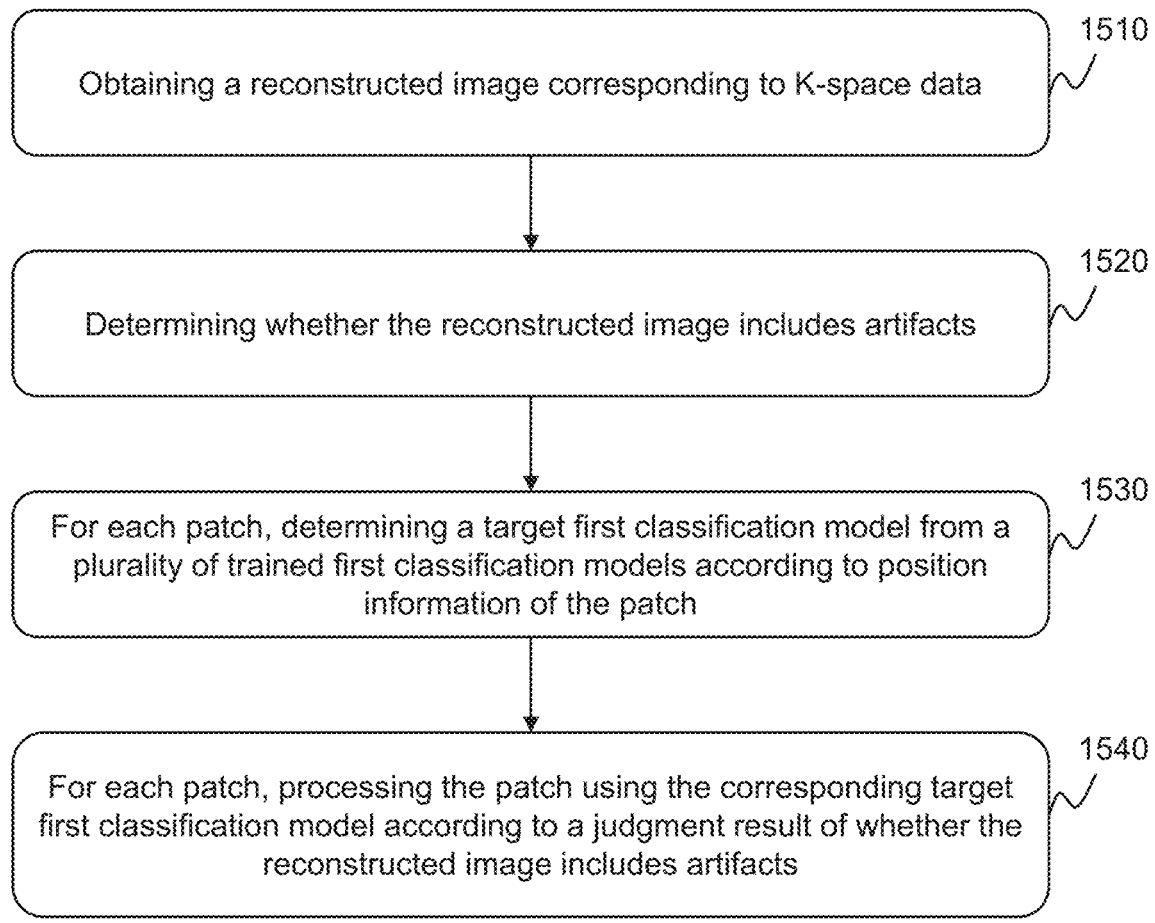
FIG. 15 is a schematic diagram illustrating an exemplary process of determining one or more target patches according to some other embodiments of the present disclosure.

FIGS. 13-15 are schematic diagrams illustrating exemplary processes of determining one or more target patches according to some embodiments of the present disclosure.

In some embodiments, process 1300, process 1400, and process 1500 may be performed by the calibration system 100. For example, the process 1300, the process 1400, or the process 1500 may be implemented as an instruction (e.g., an application program) and stored in a storage device (e.g., the storage device 140 or an external storage device of the calibration system 100). The processing device 120 (e.g., one or more modules shown in FIG. 2) may execute instructions. When executing instructions, the processing device 120 may be configured to execute the process 1300, the process 1400, or the process 1500. The operation diagrams of the process 1300, the process 1400, and the process 1500 presented below are illustrative. In some embodiments, the process may be accomplished using one or more additional operations not described and/or one or more operations not discussed. In addition, the operations sequence is shown in FIGS. 13-15 and described below are not limiting. In some embodiments, the process 1300, the process 1400, and the process 1500 may be used to implement operation 330 in FIG. 3.

As shown in FIG. 13, the process 1300 may include the following operations.

In 1310, the processing device 120 (e.g., the acquisition module 210) may obtain a reconstructed image corresponding to K-space data.

In some embodiments, the processing device 120 may obtain the reconstructed image corresponding to the K-space data by performing inverse Fourier transformation.

In 1320, the processing device 120 (e.g., the determination module 230) may determine whether the reconstructed image includes artifacts.

In some embodiments, the processing device 120 may crop at least one image block from the reconstructed image according to a second preset parameter. Further, the processing device 120 may determine whether the reconstructed image includes artifacts using a trained second classification model based on the at least one image block.

In 1330, the processing device 120 (e.g., the determination module 230) may determine multiple sets of input data based on position information of the plurality of patches in the K-space data.

In some embodiments, the processing device 120 may determine two or more patches that are positionally related to be in the same set of the input data. More descriptions about the determination of whether the reconstructed image includes artifacts and the determination of multiple sets of input data can be found in FIG. 3 (e.g., operation 330 and relevant descriptions thereof), which may not be repeated here.

In 1340, the processing device 120 (e.g., the determination module 230) may determine the target patch(es) by processing the multiple sets of input data using the trained first classification model, respectively, according to the judgment result of whether the reconstructed image includes artifacts.

In some embodiments, when the reconstructed image includes artifacts, the processing device 120 may determine that the K-space data includes abnormal points. When the reconstructed image does not include artifacts, the processing device 120 may determine that the K-space data does not include abnormal points. In some embodiments, the processing device 120 may adjust a preset threshold of the at least one trained first classification model according to the judgment result of whether the reconstructed image includes artifacts. The preset threshold may be used to determine whether a patch is a target patch including abnormal points. For example, when the reconstructed image does not include artifacts, the processing device 120 may adaptively increase the preset threshold. Further, the processing device 120 may input the multiple sets of input data into the at least one adjusted trained first classification model to determine the target patch(es).

As shown in FIG. 14, in some embodiments, the process 1400 may include operations 1410 to 1450.

In 1410, the processing device 120 (e.g., the acquisition module 210) may obtain a reconstructed image corresponding to K-space data.

In 1420, the processing device 120 (e.g., the determination module 230) may determine whether the reconstructed image includes artifacts. Operation 1410 and operation 1420 are similar to operation 1310 and operation 1320 in the process 1300 respectively.

In 1430, the processing device 120 (e.g., the determination module 230) may determine a preprocessing parameter of each patch according to position information of the patch in the K-space data.

In 1440, for each patch, the processing device 120 (e.g., the calibration module 240) may preprocess the patch based on the preprocessing parameter of the patch to obtain the preprocessed patch. More descriptions regarding the preprocessing of a patch may refer to the relevant descriptions of operation 330, which may not be repeated here.

In 1450, the processing device 120 (e.g., the calibration module 240) may process the preprocessed patches using a trained first classification model according to a judgment result of whether the reconstructed image includes artifacts to determine the target patch(es).

In some embodiments, when the reconstructed image includes artifacts, the processing device 120 may determine that the K-space data include abnormal points. When the reconstructed image does not include artifacts, the processing device 120 may determine that the K-space data does not include abnormal points. In some embodiments, the processing device 120 may adjust a preset classification threshold corresponding to the K-space data according to the judgment result of whether the reconstructed image includes artifacts. Further, the processing device 120 may use the adjusted trained first classification model to process the preprocessed patches to determine the target patch(es).

As shown in FIG. 15, in some embodiments, the process 1500 may include operations 1510 to 1540.

In 1510, the processing device 120 (e.g., the acquisition module 210) may obtain the reconstructed image corresponding to the K-space data.

In 1520, the processing device 120 (e.g., the determination module 230) may determine whether the reconstructed image includes artifacts. Operation 1510 and operation 1520 are similar to operations 1310 and 1320, respectively.

In 1530, for each patch, the processing device 120 (e.g., the determination module 230) may determine a target first classification model from a plurality of trained first classification models according to the position information of the patch.

In 1540, for each patch, the processing device 120 (e.g., the calibration module 240) may process the patch using the target first classification model of the patch according to the judgment result of whether the reconstructed image includes artifacts to determine the target patch(es).

In some embodiments, for a patch, the processing device 120 (e.g., the calibration module 240) may adjust a preset threshold of the corresponding target first classification model according to the judgment result of whether the reconstructed image includes artifacts. The preset threshold may be used to determine whether a patch is a target patch including abnormal points. For example, when the reconstructed image does not include artifacts, the processing device 120 (e.g., the calibration module 240) may adaptively increase the preset threshold of the target first classification model. Further, the processing device 120 may input the patch into the adjusted target first classification model.

It should be noted that the above description of the process 1300, the process 1400, and the process 1500 is provided for illustrative purposes only and is not intended to limit the scope of the present disclosure. For those skilled in the art, various changes and modifications may be made according to the description of the present disclosure. For example, in process 1400, the processing device 120 may execute operation 1410 and operation 1430 at the same time, or first, execute operations 1430-1440, and then execute operations 1410-1420. However, these changes and modifications do not depart from the scope of the present disclosure.

The possible beneficial effects of the embodiments of the present disclosure may include but are not limited to: (1) The imaging data may be divided into a plurality of patches, and whether the imaging data includes abnormal points may be determined based on the plurality of patches. This may reduce the data processing load of the calibration system, reduce the misjudgment of abnormal points, and improve the accuracy of abnormal point detection; (2) Artifact calibration may be performed based on patch(es) include abnormal points (i.e., target patch(es)), which may improve the efficiency and accuracy of the artifact calibration and save time cost; (3) Whether the K-space data includes abnormal points may be determined based on a determination result of whether a corresponding reconstructed image includes artifacts. In such cases, K-space data that includes unobvious artifacts may be omitted from subsequent processing or calibration, which reduces unnecessary calibration operations, and improves the accuracy of the abnormal point recognition and the efficiency of artifact calibration; (4) By adopting different processing strategies for patches in different areas of the K-space, misjudgment of abnormal points can be reduced and the accuracy of data calibration can be improved; (5) By determining the exact positions of abnormal points (such as spark points) in the imaging data (such as the K-space data) and calibrating the imaging data based on the positions of the abnormal points, a magnetic resonance image without spark artifacts can be generated based on the calibrated imaging data, so as to improve the diagnosis efficiency and the accuracy of diagnosis results. It should be noted that different embodiments may produce different beneficial effects. In different embodiments, the possible beneficial effects can be any one or a combination of the above or any other possible beneficial effects.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by this disclosure and are within the spirit and scope of the exemplary embodiments of this disclosure.

Meanwhile, certain terminology has been used to describe embodiments of the present disclosure. For example, the terms "one embodiment," "an embodiment," and/or "some embodiments" mean that a particular feature, structure, or characteristic described in connection with the embodiment is in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in smaller than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A calibration method implemented on a computing device having at least one processor and at least one storage device, comprising:
    obtaining imaging data, the imaging data including K-space data collected by magnetic resonance imaging (MRI) device;
    dividing the imaging data into a plurality of patches, each of the plurality of patches including multiple data points of the imaging data;
    determining one or more target patches from the plurality of patches by processing the plurality of patches using at least one trained machine learning model, wherein the one or more target patches are part of the plurality of patches and each target patch includes one or more abnormal points;
    calibrating the imaging data by calibrating the one or more target patches to obtain calibrated imaging data; and
    generating a magnetic resonance image based on the calibrated imaging data.

2. The calibration method of claim 1, wherein
    the determining the one or more target patches from the plurality of patches by processing the plurality of patches using at least one trained machine learning model comprises;
    processing the plurality of the patches using at least one trained first classification model to obtain an output of the at least one trained first classification model; and
    determining the one or more target patches from the plurality of patches based on the output.

3. The calibration method of claim 2, wherein the at least one trained first classification model includes a Vision Transformer deep learning model.

4. The calibration method of claim 2, wherein the processing the plurality of patches using at least one trained first classification model to obtain an output of the at least one trained first classification model comprises:
    for each patch of the plurality of patches,
        determining a preprocessing parameter of the patch based on position information indicating a position of the patch in the imaging data; and
        preprocessing the patch based on the preprocessing parameter of the patch to obtain a preprocessed patch; and processing the plurality of preprocessed patches using the at least one trained first classification model to obtain an output of the at least one trained first classification model.

5. The calibration method of claim 2, wherein the at least one trained first classification model includes a plurality of trained first classification models corresponding to different positions of K-space, the processing the plurality of patches using at least one trained first classification model comprises:

for each of the plurality of patches,
selecting, from the plurality of trained first classification models, a trained first classification model corresponding to the patch based on position information of the patch in the imaging data; and
processing the patch using the selected trained first classification model.

6. The calibration method of claim 2, wherein the processing the plurality of the patches using at least one trained first classification model comprises:

processing the plurality of patches and position information of the plurality of patches in the imaging data using the at least one trained first classification model.

7. The calibration method of claim 6, wherein
the at least one trained first classification model includes a convolutional neural network (CNN) model that includes a position encoding component integrated into a fully connected layer of the CNN model, the position information is processed using the position encoding component, or
the at least one trained first classification model includes a vision transformer (VIT) deep learning model that includes a transformer encoder layer, the position information is processed using the transformer encoder layer.

8. The calibration method of claim 2, wherein the output of the at least one trained first classification model includes a probability value that each patch includes abnormal points,
the one or more target patches are determined from the plurality of patches based on the probability value and a preset classification threshold corresponding to each patch, preset classification thresholds corresponding to the patches at different positions in the imaging data are different.

9. The calibration method of claim 8, wherein a preset classification threshold corresponding to a patch located in a central area of the K-space is greater than a preset classification threshold corresponding to a patch located in other areas of the K-space.

10. The calibration method of claim 1, wherein the determining the one or more target patches from the plurality of patches by processing the plurality of patches using at least one trained machine learning model comprises:
generating a reconstructed image based on the K-space data;
determining whether the reconstructed image includes artifacts; and
determining the one or more target patches by processing the plurality of patches using at least one trained first classification model based on a determination result of whether the reconstructed image includes artifacts.

11. The calibration method of claim 10, wherein the determining whether the reconstructed image includes artifacts comprises:
cropping at least one image block from the reconstructed image; and
determining whether the reconstructed image includes artifacts by processing the at least one image block using a trained second classification model.

12. The calibration method of claim 1, wherein the calibrating the imaging data by calibrating the one or more target patches to obtain calibrated imaging data comprises:
obtaining one or more calibrated target patches by calibrating the one or more target patches using a trained artifact calibration model;
calibrating the imaging data based on the one or more calibrated target patches to obtain the calibrated imaging data.

13. The calibration method of claim 1, wherein the calibrating the imaging data by calibrating the one or more target patches to obtain calibrated imaging data comprises:
segmenting the one or more abnormal points from the one or more target patches by using an abnormal point segmentation model; and
calibrating the imaging data based on a segmentation result of the one or more abnormal points to obtain the calibrated imaging data.

14. The calibration method of claim 1, wherein the determining the one or more target patches from the plurality of patches by processing the plurality of patches using the at least one trained machine learning model comprises:
determining multiple sets of input data based on position information indicating positions of the plurality of patches in the imaging data; and
determining the one or more target patches by inputting the multiple sets of input data into at least one trained first classification model, respectively.

15. The calibration method of claim 1, wherein the at least one trained machine learning model includes a trained patch calibration model, the one or more target patches are determined and calibrated by inputting the plurality of patches into the trained patch calibration model.

16. The calibration method of claim 15, further comprising:
determining multiple sets of input data based on position information indicating positions of the plurality of patches in the imaging data, wherein the one or more target patches are determined and calibrated by inputting the multiple sets into the trained patch calibration model, respectively.

17. The calibration method of claim 1, wherein the dividing the imaging data into a plurality of patches comprises:
obtaining a preset parameter relating to at least one of the size or the shape of the plurality of patches;
dividing the imaging data into the plurality of patches based on the preset parameter.

18. The calibration method of claim 1, wherein each of the one or more target patches is calibrated by:
for each abnormal point of the one or more abnormal points in the target patch,
determining a reference position of the abnormal point based on a position of the target patch in the imaging data;
determine position information of the abnormal point in the imaging data based on the reference position of the abnormal point; and
calibrating the target patch based on the position information of the one or more abnormal points.

19. A calibration system, comprising:
at least one storage device storing a set of instructions; and at least one processor configured to communicate with the at least one storage device, wherein when executing the set of instructions, the at least one processor is configured to direct the system to:

obtain imaging data, the imaging data including K-space data collected by magnetic resonance imaging (MRI) device;

divide the imaging data into a plurality of patches, each of the plurality of patches including multiple data points of the imaging data;

determine one or more target patches from the plurality of patches by processing the plurality of patches using at least one trained machine learning model, wherein the one or more target patches are part of the plurality of patches and each target patch includes one or more abnormal points;

calibrate the imaging data by calibrating the one or more target patches to obtain calibrated imaging data; and generate a magnetic resonance image based on the calibrated imaging data.

20. A non-transitory computer-readable storage medium, comprising instructions that, when executed by at least one processor, direct the at least processor to perform a calibration method, the calibration method comprising:

obtaining imaging data, the imaging data including K-space data collected by magnetic resonance imaging (MRI) device;

dividing the imaging data into a plurality of patches, each of the plurality of patches including multiple data points of the imaging data;

determining one or more target patches from the plurality of patches by processing the plurality of patches using at least one trained machine learning model, wherein the one or more target patches are part of the plurality of patches and each target patch includes one or more abnormal points;

calibrating the imaging data by calibrating the one or more target patches to obtain calibrated imaging data; and generating a magnetic resonance image based on the calibrated imaging data.

* * * * *